United States Patent [19]

Oumi et al.

[11] Patent Number: 4,648,385

[45] Date of Patent: Mar. 10, 1987

[54] APPARATUS FOR DRIVING A MEDICAL APPLIANCE

[75] Inventors: Takeharu Oumi; Toshinobu Kageyama, both of Toyota; Sadahiko Mushika, Tokyo, all of Japan

[73] Assignee: Aisin Seiki Kabushiki Kaisha, Aichi, Japan

[21] Appl. No.: 671,384

[22] Filed: Nov. 14, 1984

[30] Foreign Application Priority Data

Nov. 14, 1983 [JP] Japan .................................. 58-213748

[51] Int. Cl.$^4$ ............................................ A61B 19/00
[52] U.S. Cl. ..................................................... 128/1 D
[58] Field of Search .................. 128/1 D, 204.19; 3/1, 3/1.7

[56] References Cited

U.S. PATENT DOCUMENTS

| | | | |
|---|---|---|---|
| 3,234,932 | 2/1966 | Bird et al. | 128/204.19 |
| 3,410,263 | 11/1968 | McGinnis | 128/1 D |
| 3,452,738 | 6/1969 | Jones | 128/1 D |
| 3,550,162 | 12/1970 | Huffman et al. | 3/1 |
| 3,572,979 | 3/1971 | Morton | 128/1 D |
| 3,698,381 | 10/1972 | Federico et al. | 128/1 D |
| 3,955,557 | 5/1976 | Takagi | 128/1 D |
| 3,966,358 | 6/1976 | Heimes | 3/1.7 |
| 4,080,958 | 3/1978 | Bregman | 128/1 D |
| 4,175,264 | 11/1979 | Schiff | 128/1 D |

FOREIGN PATENT DOCUMENTS 2524318  3/1983  France .................................. 128/1 D Primary Examiner—Kyle L. Howell
Assistant Examiner—David Shay
Attorney, Agent, or Firm—Sughrue, Mion, Zinn, Macpeak and Seas

[57] ABSTRACT

With a driving system being separated by a diaphragm into two sections, a predetermined pressure is applied to the primary side of the diaphragm using air and helium gas or the like is used on the secondary side of the diaphragm, so that the pressure on the primary side of the diaphragm is transmitted to an artificial heart or the like connected to the secondary side thereof. Independently of a control system for maintaining the output from a pressure sensor to a predetermined value at all times, a solenoid valve for directly providing a higher pressure produced by a compressor or the like at the given drive timing is provided in a pressure regulating system, thereby causing a sharp rise in drive of the diaphragm. In an operation mode for automatically exhausting air from the secondary side of the diaphragm, the higher and lower pressures are alternately applied to the secondary side with the primary side being subject to the lower pressure, thus replacing air by another gas.

16 Claims, 32 Drawing Figures

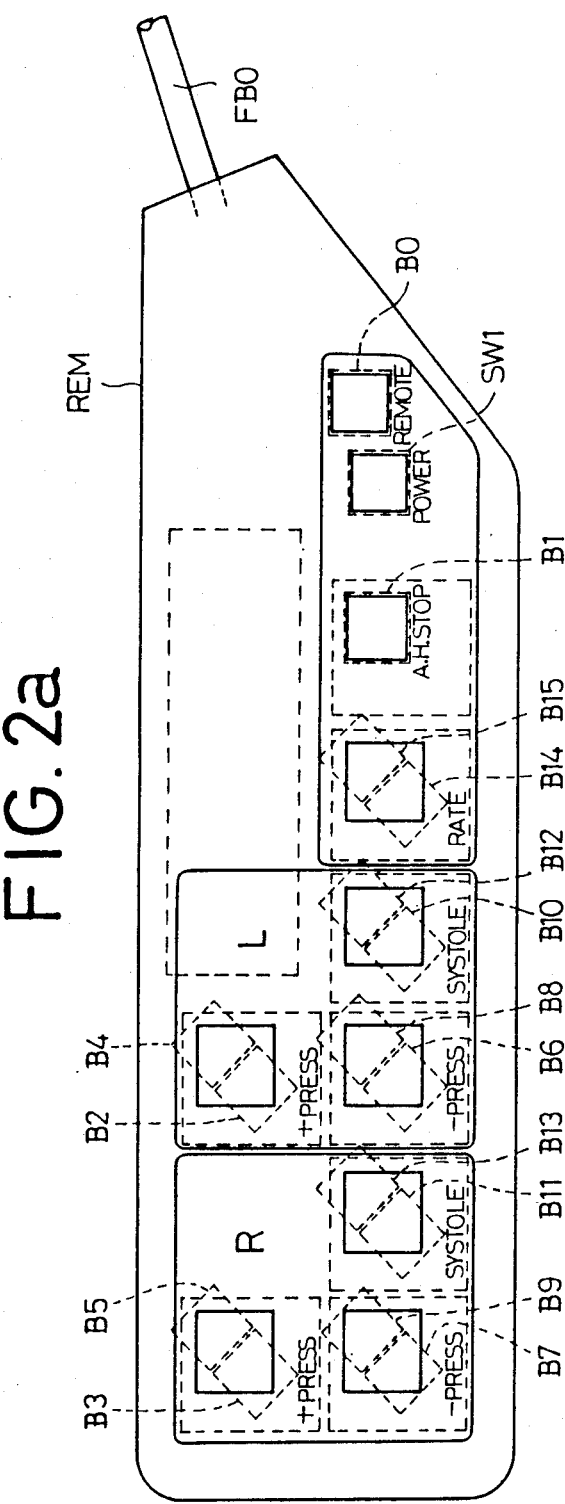
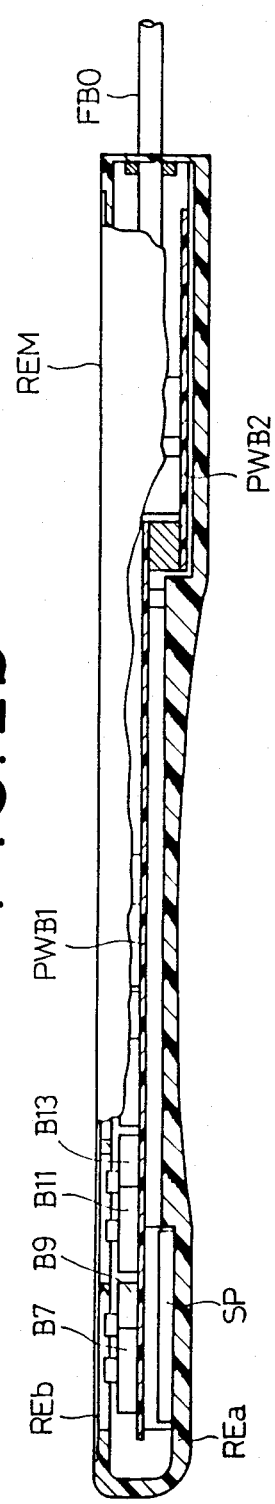

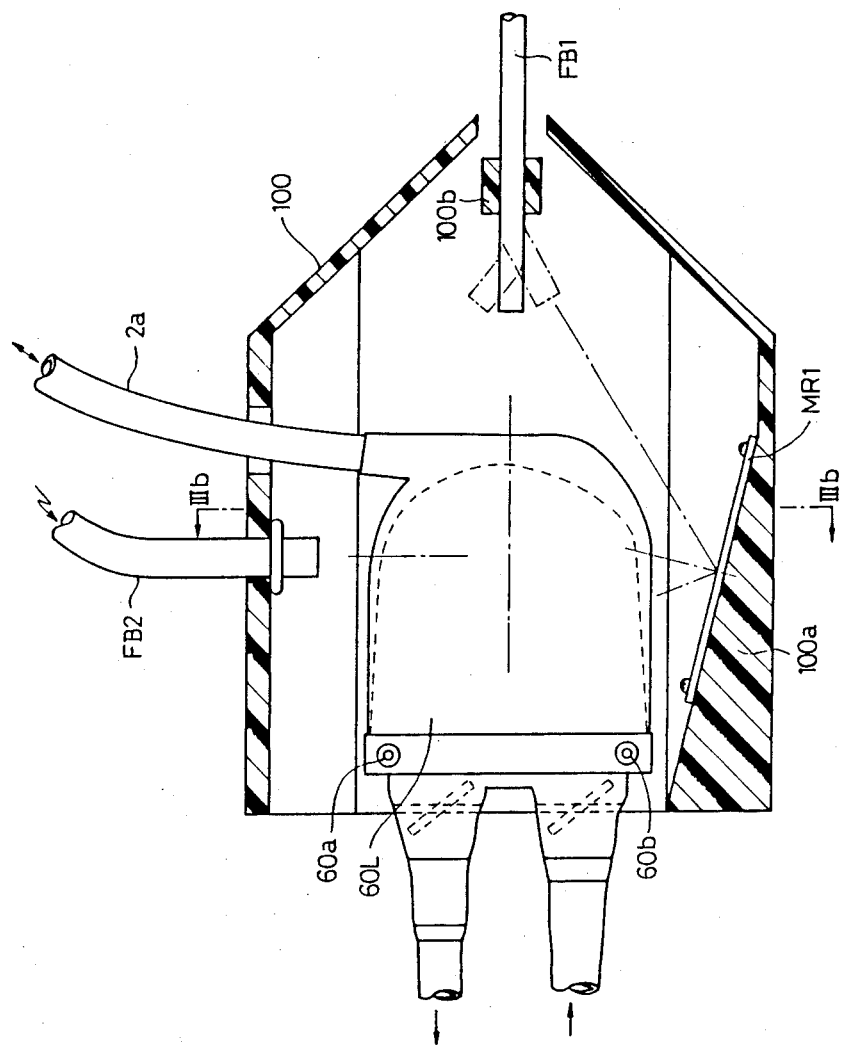

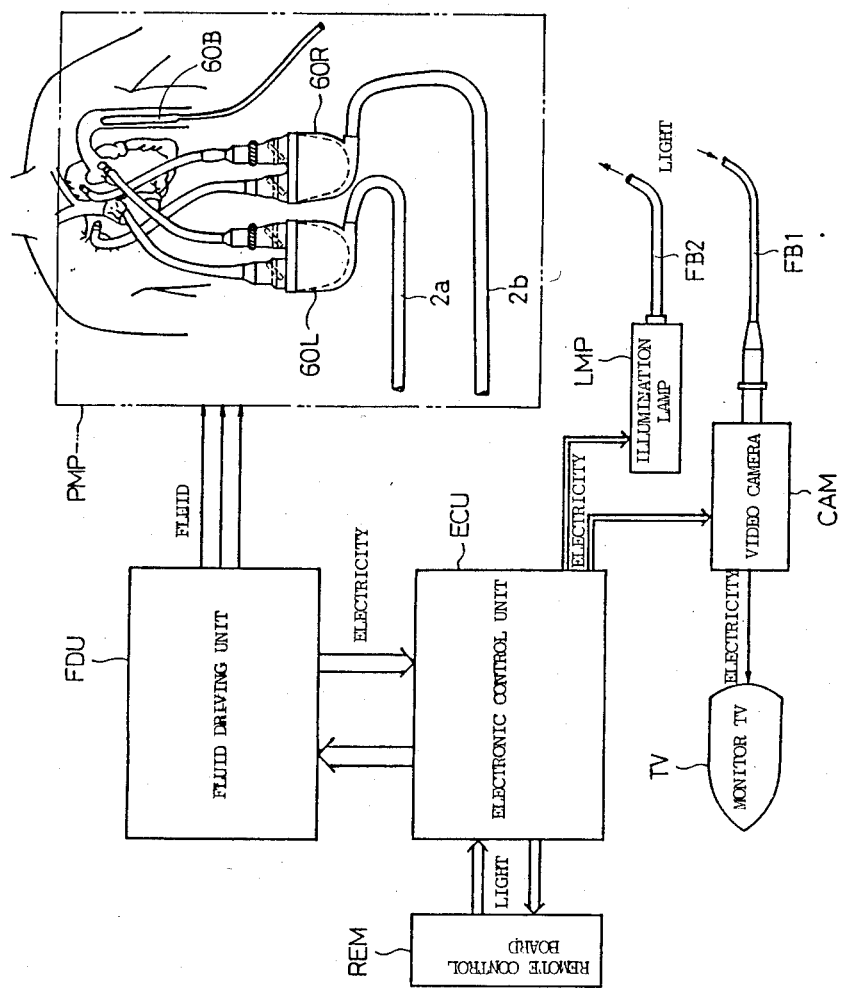

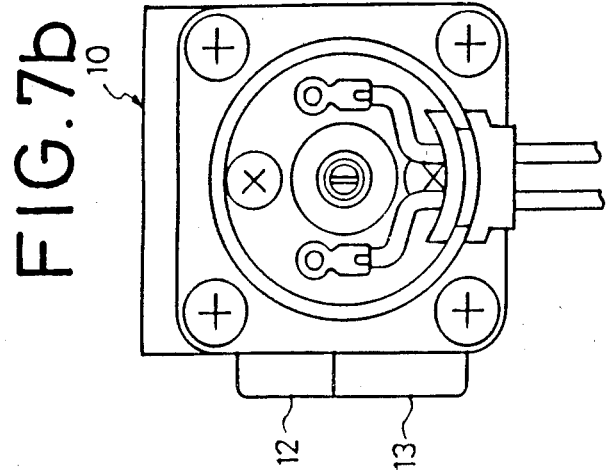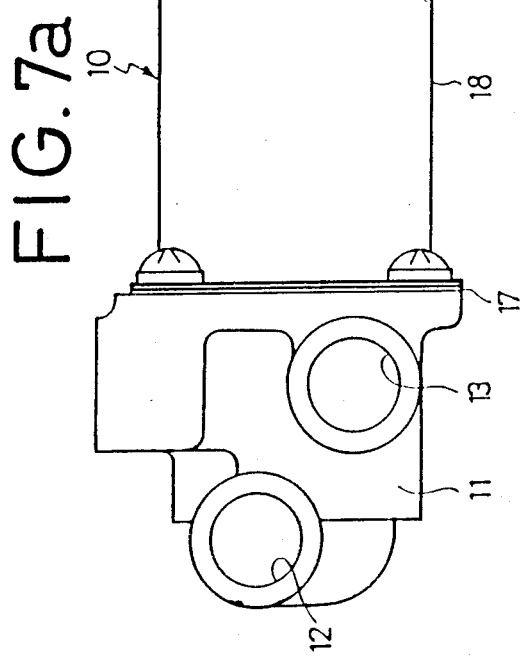

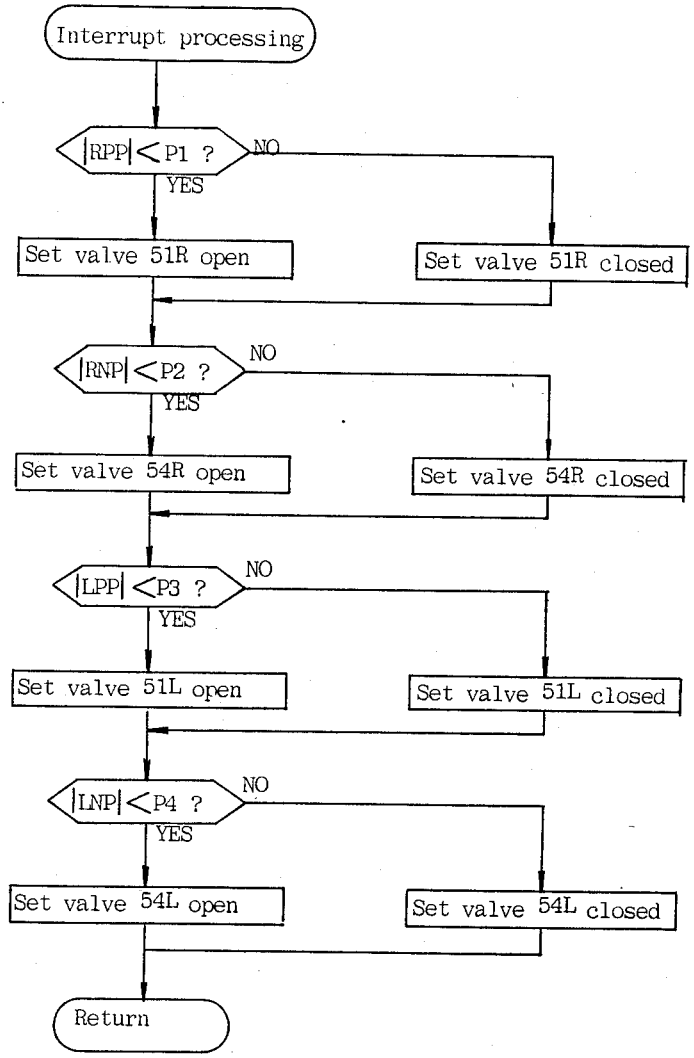

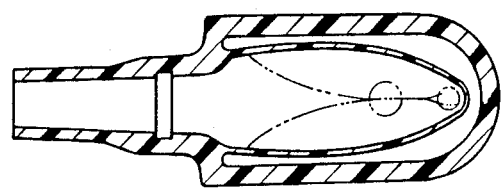
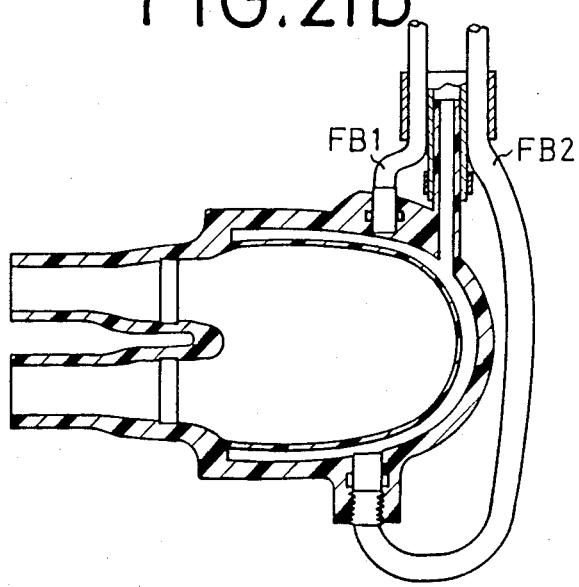

APPARATUS FOR DRIVING A MEDICAL APPLIANCE

BACKGROUND OF THE INVENTION

The present invention relates to an apparatus for driving a medical appliance such as an artificial heart or balloon pump in the main artery, and more particularly to a fluid driving apparatus for regularly changing a fluid pressure in accordance with the instructed parameter.

From the standpoint of safety, it is important for an artificial heart to be driven to give blood with a pulsatory current which is closely analogous to pulsation of a heart in the living body. There are known various artificial hearts of diaphragm type, sack type, piston type, etc., which are generally driven by receiving the predetermined pressure from a fluid such as air. In order to drive the artificial heart under the optimum conditions best suitable for the state of the living body, a driving apparatus is required which can output a precise pressure in accordance with those conditions at the given timing. In other words, the driving apparatus is preferably capable of setting all parameters such as heart rate, positive (plus) pressure, negative (minus) pressure, duration or duty ratio for applying the positive and negative pressure to the artificial heart, etc. to the respective predetermined values precisely and promptly.

In the conventional driving apparatus for an artificial heart, mechanical pressure reducing valves or the like are employed in the positive and negative pressure systems separately to serve as means for obtaining the desired precise pressures. However, in the usual driving apparatus for an artificial heart an output terminal of the positive pressure system is interconnected with an output terminal of the negative pressure system, so that the negative pressure becomes a load of the positive pressure system and the positive pressure becomes a load of the negative pressure system. This results in such a disadvantage that, upon adjusting the negative pressure, for example, the load of the positive pressure system is changed correspondingly and hence the positive pressure is also changed, and upon adjusting the positive pressure, the load of the negative pressure system is changed correspondingly and hence the negative pressure is also changed. In the past, therefore, even when adjusting one pressure, it must be carefully adjusted such that two pressure reduction regulating valves are simultaneously operated while confirming two pressure readings, and one pressure is updated while keeping the other pressure at a predetermined value. This leads to a defect in that pressure adjustment requires a great deal of skill and is time consuming.

In view of the above, the applicant of this patent application has previously proposed an artificial heart driving apparatus (U.S. patent application Ser. No. 480,181) in which solenoid valves for regulating pressures are provided in the positive and negative pressure systems, respectively, thereby achieving highly accurate pressure adjustment and facilitating setting of various parameters In the artificial heart driving apparatus of this type, since the positive and negative pressures are alternately applied to the artificial heart, a fluid must be alternately applied and discharged, whereby a large amount of driving fluid is consumed. Accordingly, air is generally used as a driving fluid.

In an artificial heart driven with a fluid, however, the driving fluid is separated from blood by just a thin film. Thus, if the artificial heart should fail, the driving fluid may leak through the thin film. In such an event, if air is used as a driving fluid, blood is coagulated and this endangers the patient's life.

SUMMARY OF THE INVENTION

A first object of the present invention is to provide a driving apparatus free from danger, which produces no adverse influence on the patient's life even if a medical appliance such as an artificial heart should undergo any anomaly, e.g., leakage of a fluid.

To eliminate the possible danger relating to a fluid leak in the artificial heart, those fluids which have the property of safety for blood, such as helium gas or carbon dioxide, for example, may be used as a driving fluid. But, since a large amount of fluid is consumed to run pressure adjustment, a large-sized helium tank must be prepared, thus increasing the size of the apparatus as a whole, if helium gas is used throughout the entire system. In the present invention, therefore, at least one diaphragm is arranged in a driving system to divide the fluid driving system into plural sections, air or the like is used in the pressure regulating system, and a fluid free from danger, such as helium gas, is used in the system for directly driving an artificial heart According to the experiment made by the present inventors, in case the driving system is divided into plural sections and an artificial heart is driven using both air and helium gas or the like, there could not be obtained the good satisfactory driving result by a driving apparatus which has the prior art construction. More specifically, it was found that, although positive and negative pressures must be alternately switched over in an artificial heart at the given timing in accordance with heart rate, changes in the waveform of pressure lost sharpness at both rising of the switched pressure (switching from negative pressure to positive pressure) and falling thereof (switching from positive pressure to negative pressure) and hence an amount of sendable blood was decreased.

In such pressure regulating system of the driving apparatus, since a large amount of air is consumed at the time of switching between the positive pressure and the negative pressure, an accumulator is usually provided in each of the positive and negative pressure systems for storing a fluid separately, thereby to prevent a substantive reduction in pressure as well as to stabilize the level of pressure. Even by so doing, however, it is difficult to prevent a reduction in pressure, unless an accumulator of very large capacity is used. Meanwhile, use of an accumulator requires a lot of time for pressure to be returned back to the original level after it is changed. As a result, it is difficult to obtain the squared waveform of pressure which can ensure prompt switching between the positive pressure and the negative pressure.

It is a second object of the present invention to provide a driving apparatus which is capable of producing the squared waveform of pressure to ensure prompt switching between the positive pressure and the negative pressure.

To achieve the above second object, in a preferred embodiment of the present invention, one compensating solenoid valve separated from an accumulator is connected to at least a positive pressure system in a pressure regulating mechanism in parallel to the latter, and it is controllably opened and closed at the given timing so as to compensate a reduction in pressure. With this, even when a driving system using helium gas or the like is connected to the output side of the pressure regulating mechanism for controlling air pressure, a reduction in pressure can be sufficiently compensated to provide the squared waveform of pressure.

In case of driving an artificial heart by the use of helium gas or the like, air is contained in a tube connected to an artificial heart immediately after assembling of the apparatus, unless such a special method is employed, for example, that the apparatus is assembled in a room filled with gas. Thus, even if the artificial heart is constructed to be driven with helium gas or the like, the apparatus can not produce the effect immediately after assembling thereof. In a preferred embodiment of the present invention, there is prepared an operation mode for draining air on the secondary side (artificial heart side) of the diaphragm. In this operation mode, a pressure on the primary side of the diaphragm is controlled to cause the diaphragm to move more easily, and gas is alternately supplied and discharged on the secondary side of the diaphragm. This causes a great shift of the diaphragm, thus allowing air contained in the tube to be discharged automatically.

On the other hand, a balloon pump in the main artery is applied to a patient with heart disease in addition to an artificial heart (temporary auxiliary heart), and these medical appliances are selectively used depending on the condition of the patient. Thus, it is preferable for the driving apparatus of this kind to be selectively used for either the artificial heart or the balloon pump. In one preferred embodiment of the present invention, therefore, it is so arranged that a plurality of gas control systems are commonly connected to the output side of an air pressure controller, thus permitting the artificial heart and the baloon pump to be selectively used upon operation of a switch.

BRIEF DESCRIPTION OF THE DRAWINGS

FIGS. 2a and 2b are a top plan view and a front view showing a remote control board REM, respectively.

FIG. 3a is a top plan view showing an artificial heart 60 fitted with optical fibers FB1 FB2, etc. and FIG. 3b is a sectional view taken along the line IIIb—IIIb in FIG. 3a.

FIG. 4 is a block diagram showing the system configuration of the apparatus shown in FIG. 1.

FIGS. 7a, 7b, 7c and 7d are a top plan view, right side view, left side view and an enlarged longitudinal sectional view showing the construction of a solenoid valve used in the embodiment, respectively.

FIGS. 16a and 16b are flow charts showing schematic operation of the CPU1 in FIG. 9.

FIGS. 21a and 21b are a longitudinal sectional view and a transverse sectional view showing the mounted positions of the optical fibers FB1, FB2 to the artificial heart in one modified embodiment, respectively.

DESCRIPTION OF PREFERRED EMBODIMENTS

In the following, preferred embodiments of the present invention will be described with reference to the drawings.

Figure 1:
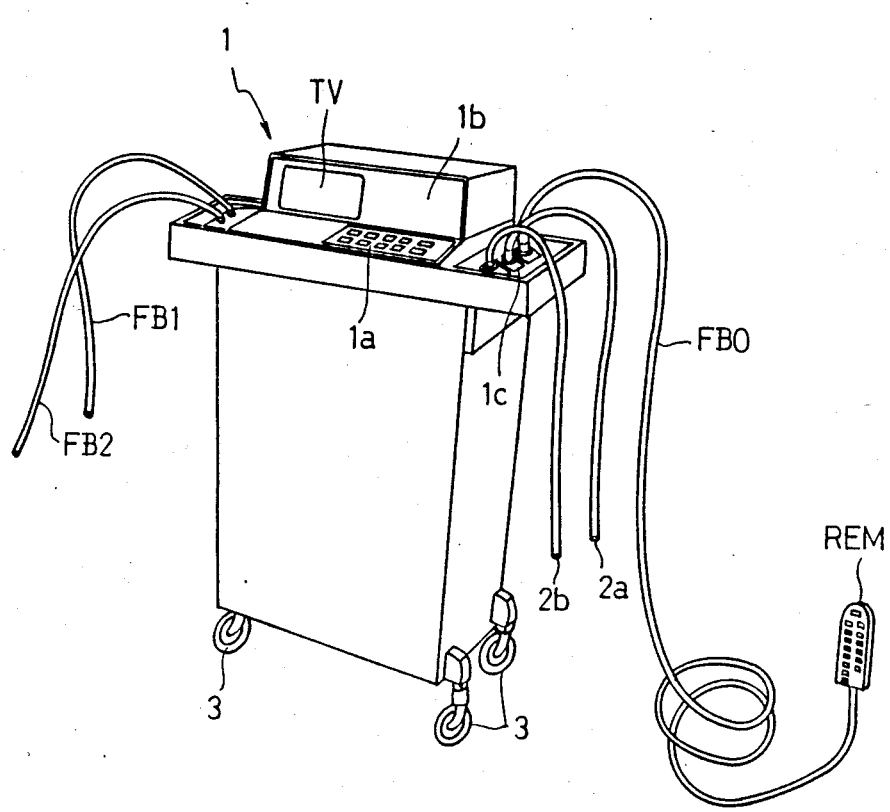
FIG. 1 is a perspective view showing a body of an artificial heart driving apparatus of one type for employing the present invention.

FIG. 1 illustrates external appearance of an artificial heart driving apparatus 1 (which is capable of driving also a balloon pump). Referring to FIG. 1, designated at 1a is a control section, at 1b is a display section and at 1c is a connecting section. Tubes 2a, 2b and an optical fiber cable FBO for remote control are connected to the connecting section 1c on the right side as looked at from front of the apparatus, and a remote control board REM is connected to the leading end of the optical fiber FBO.

Connected to the tubes 2a and 2b are artificial hearts 60L and 60R (see FIG. 4), respectively. Two optical fiber cables FB1 and FB2 are connected to the connecting section on the left side as looked at from front of the apparatus. As described later, a video camera CAM is connected to the optical fiber cable FB1 and an illumination lamp LMP is connected to the FB2. The video camera CAM and the lamp LMP are equipped for monitoring the actual operated state of the artificial hearts 60L, 60R. The display section 1b includes a monitor television unit TV for displaying an output from the video camera CAM. Designated at 3 is a caster.

FIGS. 2a and 2b illustrate the mechanical construction of the remote control board REM. Description will now be made with reference to FIGS. 2a and 2b. A case REa of the control board is formed of synthetic resin. Squared openings are formed in an upper surface of the panel at those parts corresponding to switches, so that the switches may be operated, and those parts are covered with a thin resin sheet REb. Printed circuit boards PWB1 and PWB2 are integrally connected to each other. On the printed circuit boards PWB1 and PWB2 there are arranged seventeen switches SW1 and B0 to B15, a battery, a speaker SP, an optoelectrical converter, an electrooptical converter, etc.

FIGS. 3a and 3b illustrate an artificial heart 60L and a part of a unit for monitoring the operated state thereof. Description will now be made with reference to FIGS. 3a and 3b. The artificial heart 60L is screwed to a monitor case 100 at portions 60a, 60b. In this example, the optical fiber FB1 for monitoring and the optical fiber FB2 for illumination are arranged in an orthogonal relation at positions opposite to the movable portions of the artificial heart 60L so as to extend perpendicular to the depthwise direction of the artificial heart 60L. A reflection mirror MR1 is disposed at a position opposite to the distal ends of both optical fibers FB1 and FB2. As well known in usual medical appliances, the optical fiber FB1 has a tiltable fore end and can be remotely controlled.

FIG. 4 illustrates the system configuration of the apparatus shown in FIG. 1. Referring now to FIG. 4, designated at 60L and 60R are artificial hearts, and at 60B is a balloon pump in the main artery. A fluid driving unit FDU is provided with three fluid driving output terminals. But, since there can not be practically supposed such a situation that the artificial hearts 60L, 60R and the balloon pump 60B are used simultaneously, it is arranged that only two out of those three output terminals are operable simultaneously. Connected to an electronic control unit ECU for controlling the fluid driving unit FDU are the remote control board REM, the illumination lamp LMP and the video camera CAM. A signal output terminal of the video camera is connected to the monitor television unit TV. The remote control board REM and the electronic control unit ECU are interconnected through the optical fiber cable FBO, as previously noted.

Figure 5:
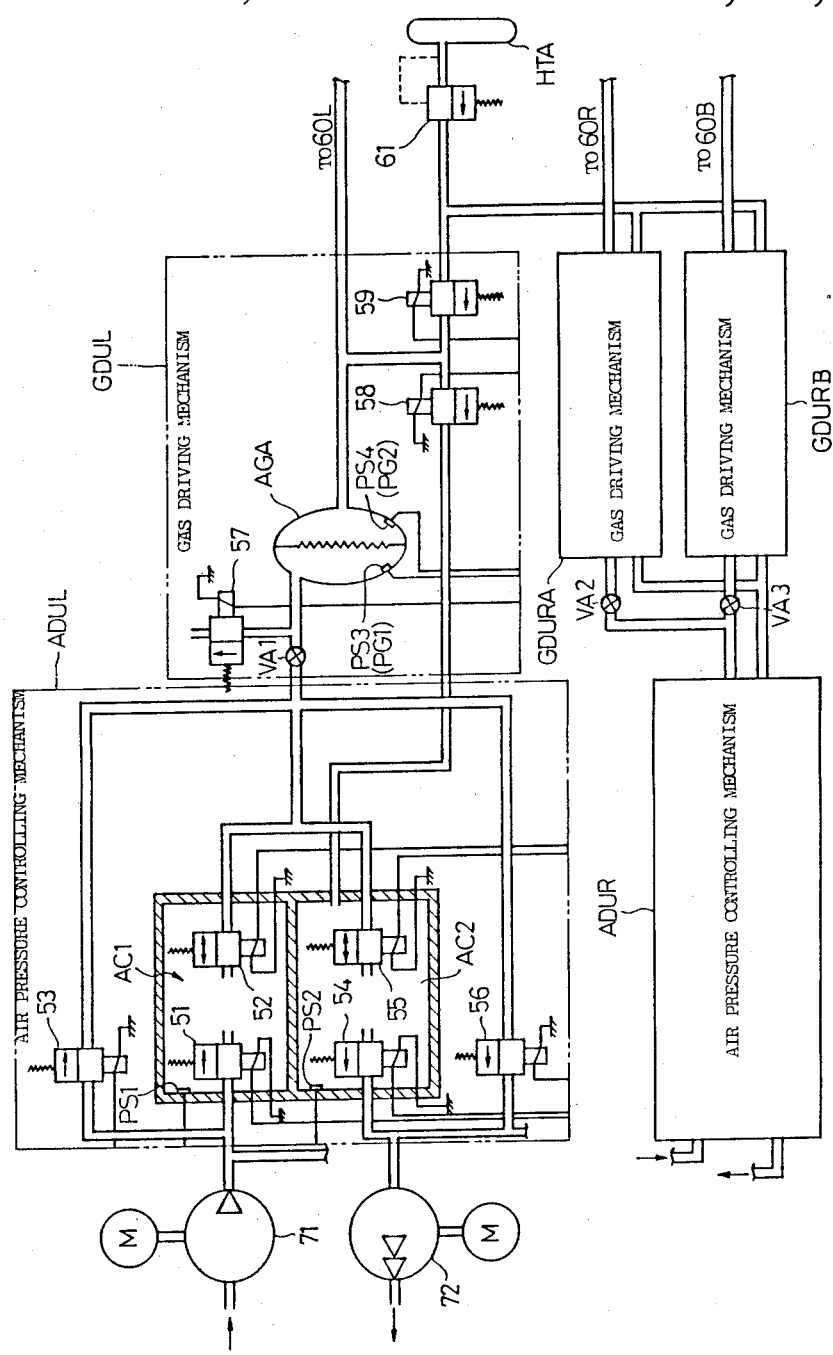
FIG. 5 is a block diagram showing the configuration of a fluid driving unit FDU shown in FIG. 4.

FIG. 5 illustrates the configuration of the fluid driving unit FDU in FIG. 4. First in brief, this unit FDU includes a compressor 71, a vacuum pump 72, air pressure controlling mechanisms ADUL and ADUR, gas driving mechanisms GDUL, GDRA and GDURB, a helium gas tank HTA, and a pressure reducing valve 61. An input terminal of the gas driving mechanism GDUL is connected to an output terminal of the air pressure controlling mechanism ADUL, while input terminals of the gas driving mechanisms GDURA and GDURB are commonly connected to an output terminal of the air pressure controlling mechanism ADUR. Output terminals of the gas driving mechanisms GDUL, GDURA and GDURB are connected to the artificial hearts 60L, 60R and the baloon pump 60B, respectively.

The air pressure controlling mechanism ADUL will now be described. This mechanism includes six solenoid valves 51, 52, 53, 54, 55 and 56. The solenoid valves 51, 52 and 53 are used for producing a positive pressure, while the solenoid valves 54, 55 and 56 are used for producing a negative pressure. The solenoid valves 51 and 52 are provided within an accumulator AC1, while the solenoid valves 54 and 55 are provided within an accumulator AC2. Input terminals of the solenoid valves 51 and 53 are connected to an output terminal of the compressor 71, input terminals (on the downstream side with respect to the running direction of a fluid) of the solenoid valves 54 and 56 are connected a negative pressure output terminal of the vacuum pump 72, and output terminals of the solenoid valves 52, 53, 55 and 56 are connected to the output terminal of the air pressure controlling mechanism ADUL. PS1 and PS2 designate pressure sensors for detecting pressures in the accumulators AC1 and AC2, respectively. The air pressure controlling mechanism ADUR has the same construction as the ADUL.

Next, the gas driving mechanism GDUL will be described. This mechanism includes solenoid valves 57, 58 and 59, a fluid isolator AGA, etc. The output terminal of the air pressure controlling mechanism ADUL is connected to the primary side (air side) of the fluid isolator AGA through a mechanical valve VA1. The solenoid valve 57 has an input terminal connected to the primary side of the fluid isolator AGA and an output terminal open to the atmosphere. The solenoid valve 59 has an input terminal connected to an output terminal of the pressure reducing valve 61 and an output terminal connected to the secondary side of the fluid isolator AGA. The solenoid valve 58 has an input terminal connected to the secondary side of the fluid isolator AGA and an output terminal connected to the inside of the accumulator AC2. The primary and secondary side of the fluid isolator AGA are provided with pressure sensors PS3 and PS4, respectively. The remaining gas driving mechanisms GDURA and GDURB have the same construction as the GDUL.

Figure 6:
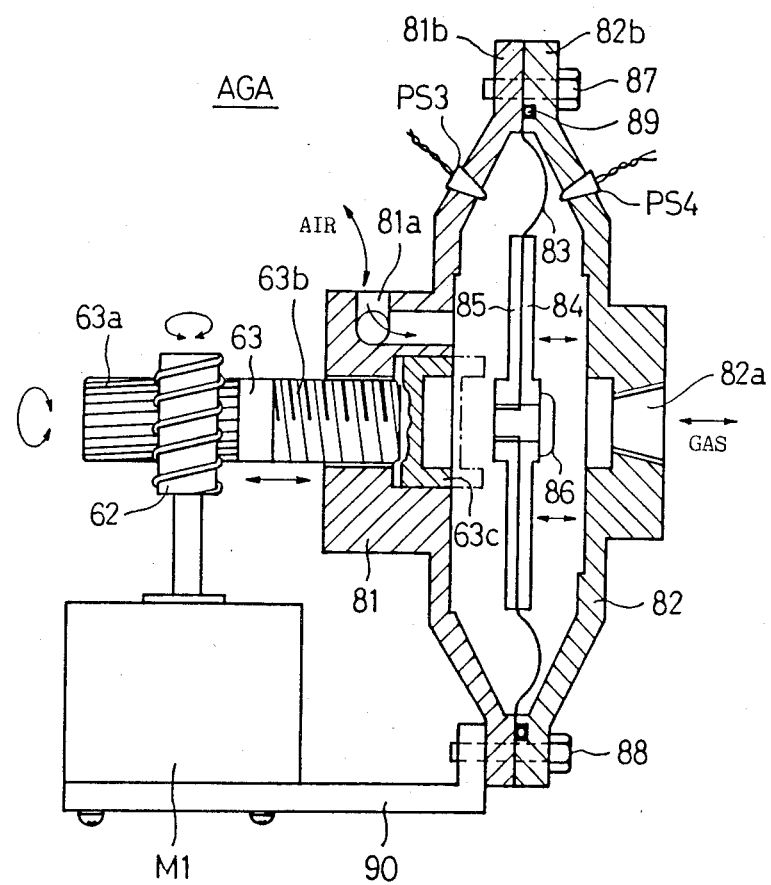
FIG. 6 is a longitudinal sectional view showing the construction of a fluid isolator AGA equipped in a gas driving mechanism GDURB in FIG. 5.
Figure 7D:
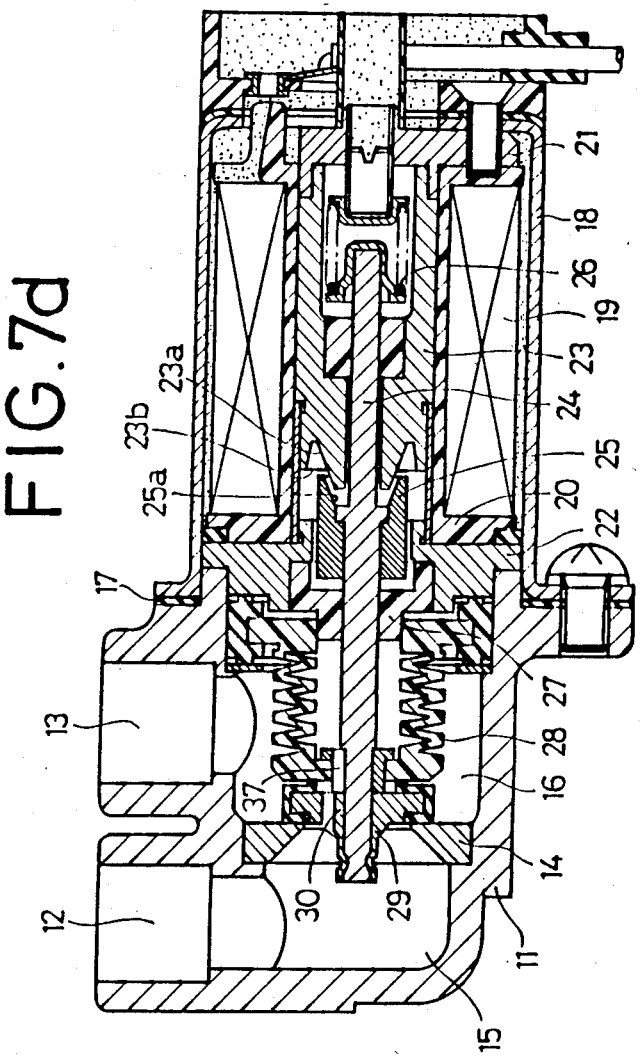
Figure 7C:
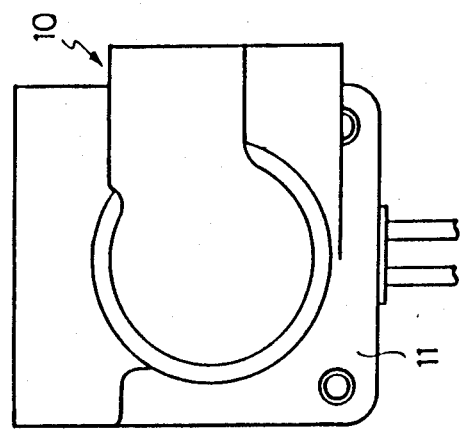

FIG. 6 illustrates the construction of the fluid isolator AGA equipped in the gas driving mechanism GDURB. Description will now be made with reference to FIG. 6. In short, the AGA is to partition the space communicating with a primary side port 81a from the space communicating with a secondary side port 82a by a diaphragm 83 held between housings 81 and 82, the diaphragm 83 being able to shift in the right and left direction in the figure.

At the center of the diaphragm 83 there are interfitted a pair of plates 84 and 85 to hold the diaphragm therebetween. Designated at 86 is a bolt for securing the plates 85 and 86. A restriction member 63 for regulating a shift amount of the plate 85 is fitted to the center of the housing 81. The restriction member 63 is formed with threads 63a and 63b, the latter thread 63b being engaged with the housing 81.

When the restriction member 63 is turned, the engaging position is changed causing the restriction member 63 to move leftwards and rightwards. The leftward movement increases a movable range of the plates 84, 85. while the rightward movement reduces a movable range of the plates 84, 85. Designated at M1 is a DC motor. Coupled to a drive shaft of the DC motor M1 is a worm gear 62, which meshes with the thread 63a. Accordingly, the movable range of the plates 84, 85 is changed by driving the motor M1. The motor M1 is secured to a flanged portion 81b of the housing 81 through a base plate 90. Designated at 89 is an O-ring and at 87, 88 are bolts for fixing the housings 81, 82.

Fluid isolators AGA equipped in the gas driving mechanisms GDUL and GDURA have the same construction as that shown in FIG. 6 except for that the motor M1 is omitted.

The solenoid valves 51, 52, 53, 54, 55, 56, 57, 58 and 59 used in this embodiment have all the same construction. A top plan view, right side view, left side view and an enlarged longitudinal sectional view of one among those solenoid valves are respectively shown in FIG. 7a, FIG. 7b, FIG. 7c and FIG. 7d. Description will now be made with reference to FIG. 7a, FIG. 7b, FIG. 7c and FIG. 7d. A valve housing 11 of the solenoid valve is formed with a first port 12 and a second port 13. An inner space of the housing 11 is partitioned by a valve seat 14 into a first inner chamber 15 communicating with the first port 12 and a second inner chamber 16 communicating with the second port 13. A coil case 18 of magnetic substance is secured to the valve housing 11 through a seal material 17.

A coil bobbin 20 having a coil 19 wound round the same is inserted in the case 18, and bases 21, 22 of magnetic substance support the coil bobbin 20. Secured to the base 21 is a fixed magnetic core 23. The core 23 is hollow and a guide rod 24 of non-magnetic substance passes therethrough. A movable magnetic core 25 is secured to the rod 24. One end of the rod 24 is pushed leftwards by means of a coil spring 26. The other end of the rod 24 extends through a bearing 27 and a bellows 28 and has a valve body 29 secured to the fore end thereof. An inner space of the bellows 28 is selectively communicated with the first inner chamber 15 (in the illustrated state) or the second inner chamber 16 (when the rod 24 is driven rightwards) through small apertures 30 and 37.

When the coil 19 is energized, it generates the magnetic flux circulating through core 23—core 25—base 22—case 18—base 21—core 23, and an attraction force toward the core 23 acts on the core 25, so that the rod 24 is moved rightwards until the attraction force is offset by a repulsion force of the coil spring 26. As a result, the valve body 29 is spaced from the valve seat 14 by a distance corresponding to the strength of the attraction force. An end face 23a of the core 23 has the W-shaped form, and an end face 25a of the core 25 is concave for receiving the central projection of the end face 23a, the inner faces 23b of both side projection of the W-shaped end face 23a being tapered. These tapered surfaces ensure the proportional relationship between the level of energization and the movement amount of the rod 24 (or the gap between 23a and 25a) in a wide range. Incidentially, the solenoid valve of this type has the movable portion with high responsivity and can be controllably opened and closed at a high speed.

Figure 8:
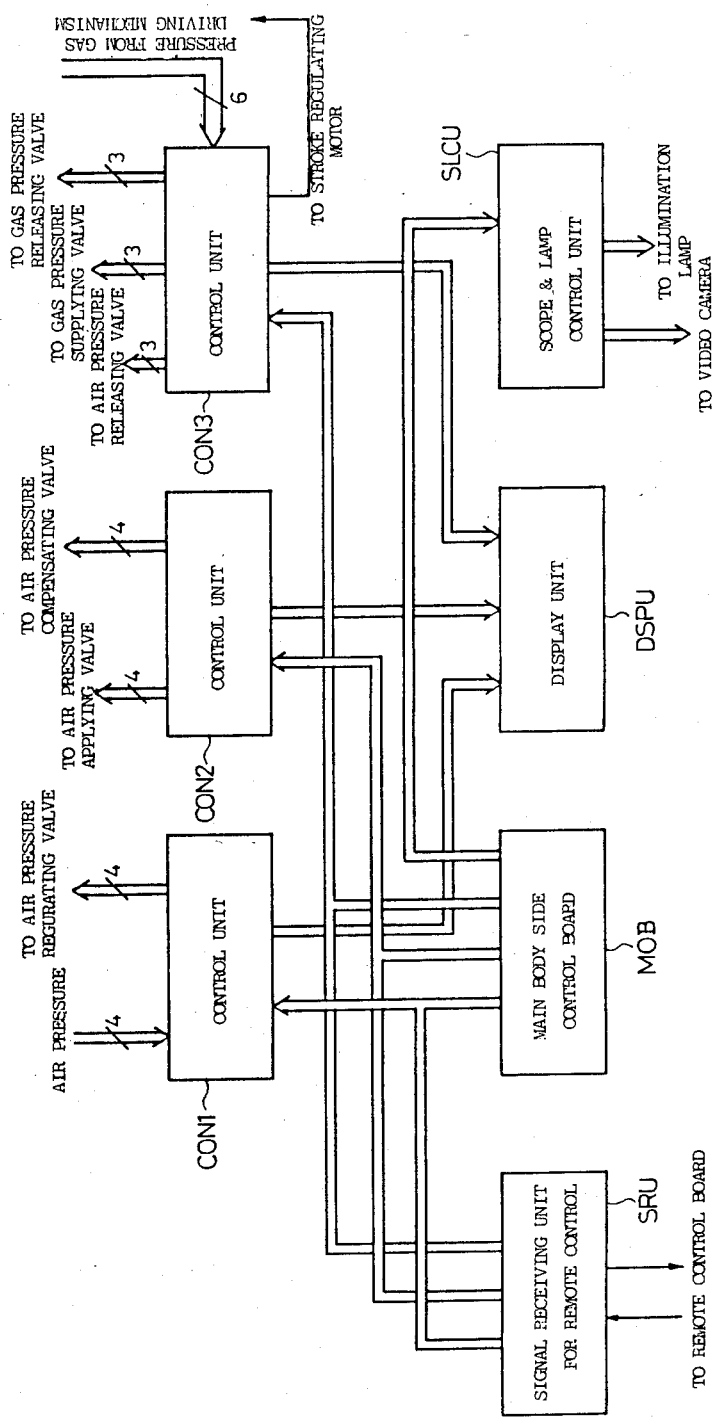
FIG. 8 is a block diagram showing the configuration of an electronic control unit ECU in FIG. 4.

FIG. 8 illustrates the configuration of the electronic control unit ECU shown in FIG. 4. Referring now to FIG. 8, the electronic control unit ECU is composed of control units CON1, CON2 and CON3, a signal receiving unit SRU for remote control, a main body side control board MOB, a display unit DSPU and a scope and lamp control unit SLCU.

The control unit CON1 monitors output signals from the pressure sensors PS1 and PS2 in the air pressure controlling mechanisms ADUL and ADUR, and then controllably open and close the solenoid valves 51 and 52 so that pressure in the accumulators AC1 and AC2 become equal to the present values.

The control unit CON2 controllably opens and closes the solenoid valves 52, 53, 55 and 56 of the air pressure controlling mechanisms ADUL and ADUR at the given timing in accordance with the preset heartbeat period, respective systolic durations (or duty ratios) for right and left artificial hearts, etc.

The control unit CON3 controls the solenoid valves 57, 58 and 59 of the gas driving mechanisms GDUL, GDURA and GDURB. It is to be noted that the GDURA and GDURB will never be controlled simultaneously. The GDUL and GDURA are controlled by monitoring output signals (PG1, PG2) from the pressure sensors PS3 and PS4, while the GDURB is controlled without monitoring the output signal from the pressure sensor PS3. During control of the GDURB, the motor M1 is controlled.

The display unit DSPU comprises a number of 7-segment indicators and is connected to the control units CON1, CON2 and CON3. The main body side control board MOB is connected to the control units CON1, CON2 and CON3 as well as the scope and lamp control unit SLCU. Output lines of the signal receiving unit SUR for remote control are connected similarly to the corresponding signal lines of the main body side control board MOB, respectively.

Figure 9:
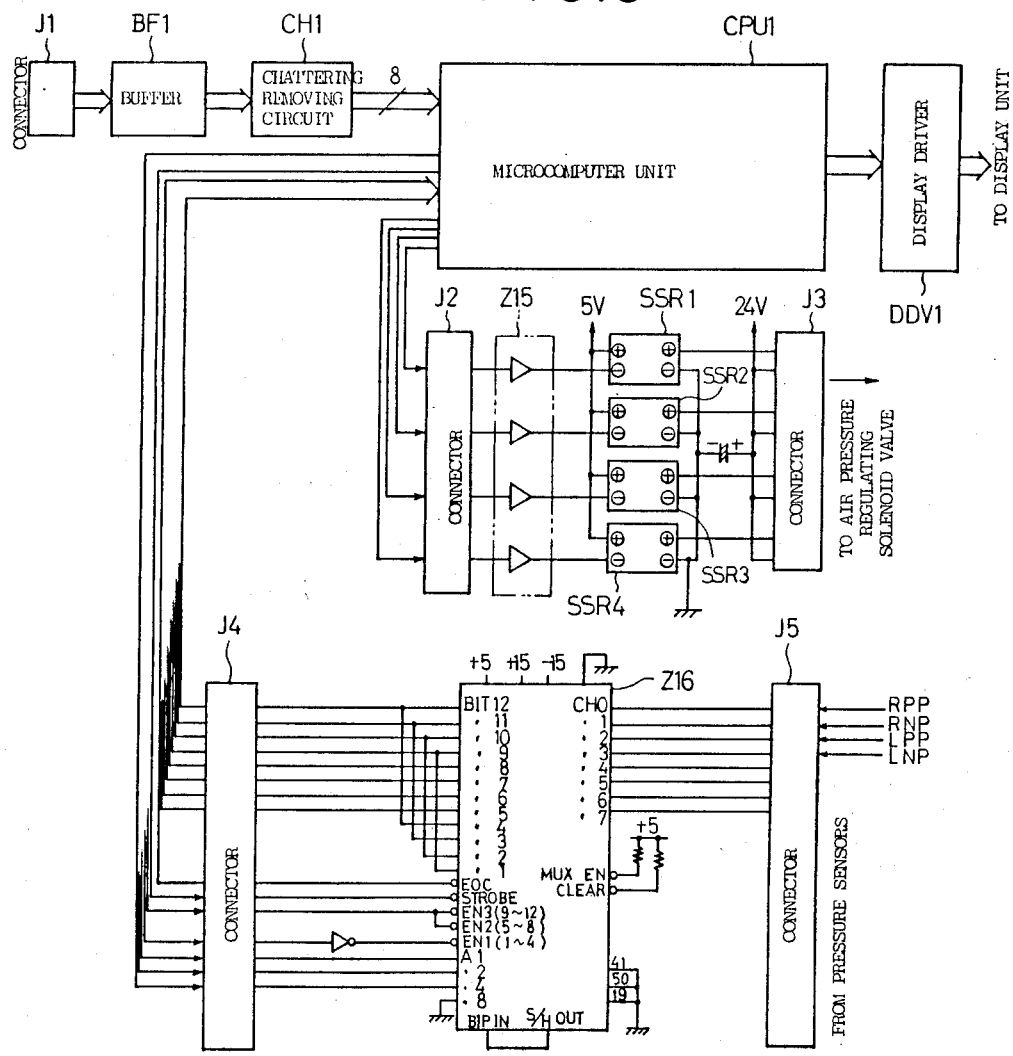
FIGS. 9, 10 and 11 are block diagrams showing the configuration of control units CON1, CON2 and CON3 in FIG. 8, respectively.

FIG. 9 illustrates the control unit CON1 of FIG. 8 in more detail. Description will now be described with reference to FIG. 9. This control unit CON1 is mainly composed of a microcomputer unit CPU1. A connector J1 to which are connected the main body side control board MOB and the signal receiving unit SRU for remote control, is in turn connected to input ports of the CPU1 through a buffer BF1 and a chattering removing circuit CH1. Signals applied to the connector J1 are of instruction signals for setting pressures such as R-side (right side) positive pressure UP, R-side positive pressure DOWN, R-side negative pressure UP, R-side negative pressure DOWN, L-side (left side) positive pressure UP, L-side positive pressure DOWN, L-side negative pressure UP, and L-side negative pressure DOWN.

Connected to four output ports of the CPU1 are solid state relays SSR1, SSR2, SSR3 and SSR4 through a buffer Z15, output terminals of which are in turn connected to the solenoid valves 51 (L, R) and 54 (L, R), respectively.

Designated at Z16 is an A/D (analog/digital) converter. This A/D converter Z16 has eight input channels, but four out of those eight input channels are used in this embodiment. Signals RPP, RNP, LPP and LNP are supplied from the pressure sensors for detecting the right side positive pressure, right side negative pressure, left side positive pressure and the left side negative pressure. Display output ports of the CPU1 are connected to the display driver DDV1, output terminals of which are in turn connected to a display unit DSPU.

Figure 10:
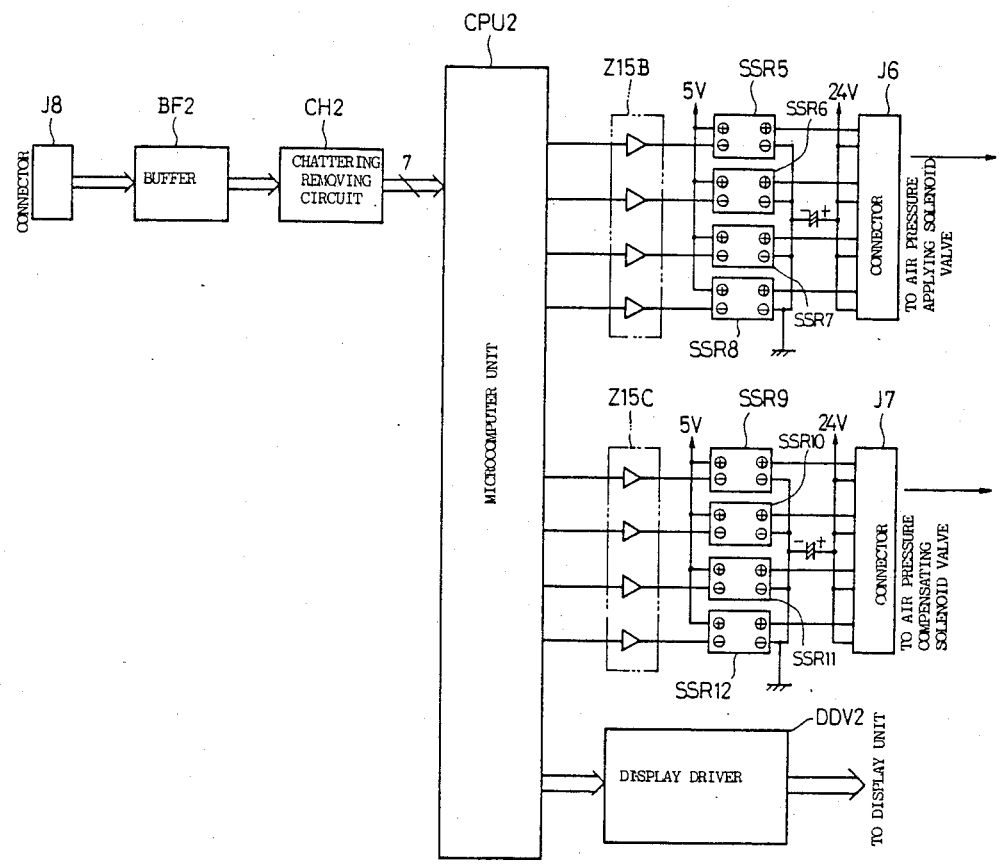

FIG. 10 illustrates the configuration of the control unit CON2 in FIG. 8. Description will now be made with reference to FIG. 10. The control unit CON2 is mainly composed of a microcomputer unit CPU2. A connector J8 to which are connected the main body side control board MOB and the signal receiving unit SRU for remote control, is in turn connected to input ports of the CPU2 through a buffer BF2 and the chattering removing circuit CH2.

Signals applied to the connector J8 are of instruction signals for setting heart rate UP, heart rate DOWN, R-side duty UP, R-side duty DOWN, L-side duty UP, L-side duty DOWN, etc. Connected to eight output ports of the CPU2 are solid state relays SSR5 to SSR12 through buffers Z15B and Z15C. The solid state relays SSR5 to SSR8 are connected to the air pressure applying solenoid valves 52 (L, R) and 55 (L, R), while the remaining SSR9 to SSR12 are connected to the air pressure compensating solenoid valves 53 (L, R) and 56 (L, R), respectively. A display driver DDV2 is connected to output ports for display signals of the CPU2, and a display unit DSPU is connected to output terminals of the DDV2.

Figure 11:
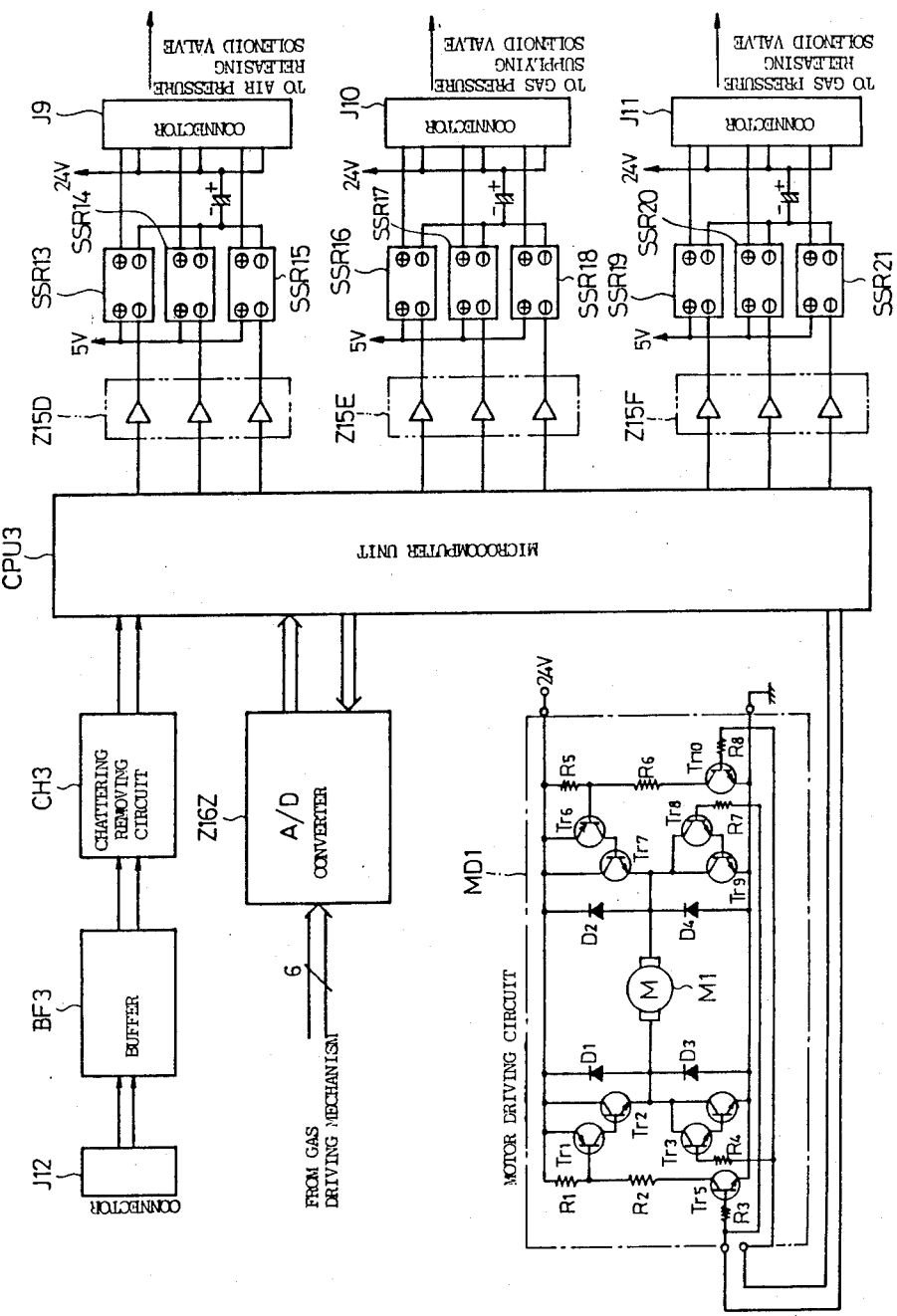

FIG. 11 illustrates the configuration of the control unit CON3 in FIG. 8. Description will now be made with reference to FIG. 11. This unit CON3 is mainly composed of a microcomputer unit CPU3. A connector J12 to which are connected the main body side control board MOB and the signal receiving unit SRU for remote control, is in turn connected to input ports of the CPU3 through a buffer BF3 and a chattering removing circuit CH3. Signals applied to the connector J12 are of an air exhausting instruction signal and an axiliary heart/balloon pump selection signal from the main side control board MOB, etc.

An A/D converter Z16B of the same construction as the Z16 is connected to the CPU3, and output terminals of the pressure sensors equipped in the gas driving mechanisms GDUL, GDURA and GDURB are connected to corresponding analog signal input terminals of the Z16B. Designated at MD1 is a circuit adapted to drive the stroke regulating motor M1. Forward rotation, backward rotation or stop of the motor M1 can be controlled by controlling two signals applied to input terminals of the MD1.

Connected to nine output ports of the CPU3 are solid state relays SSR13 to SSR21 through buffers Z15D, Z15E and Z15F. Output terminals of the SSR13, SSR14 and SSR15 are respectively connected to the solenoid valves 57 of the gas driving mechanisms GDUL, GDURA and GDURB, output terminals of the SSR16, SSR17 and SSR18 are respectively connected to the solenoid valves 59 of the gas driving mechanisms GDUL, GDURA and GDURB, and output terminals of the SSR19, SSR20 and SSR21 are respectively connected to the solenoid valves 58 of the gas driving mechanisms GDUL, GDURA and GDURB.

Figure 12:
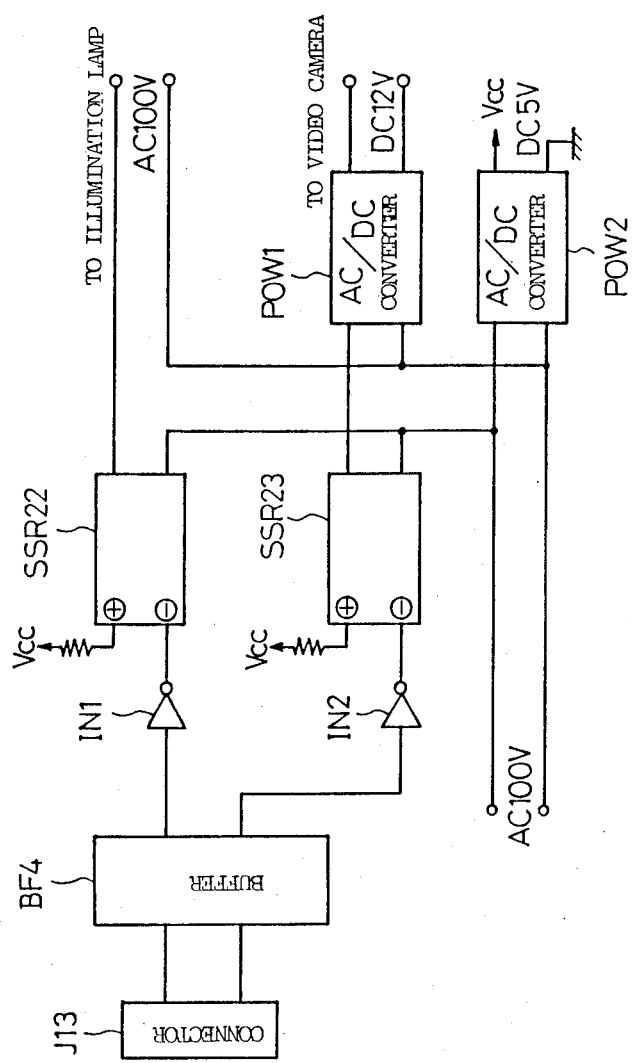
FIG. 12 is a block diagram showing the configuration of a scope and lamp control unit SLUC shown in FIG. 8.

FIG. 12 illustrates the configuration of the scope and lamp control unit SLCU in FIG. 8. This unit SLCU is composed of a buffer B4, solid state relays SSR22 and SSR23, inverters IN1 and IN2, AC/DC converters (i.e., DC power supply units) POW1, POW2, etc., output terminals of the SSR22 and the POW1 being connected to the illumination lamp LMP and the video camera CAM, respectively. The POW2 produces DC voltage used for controlling the buffer BF4, the inverters IN1, IN2 and the solid state relays SSR22, SSR23.

Figure 13:
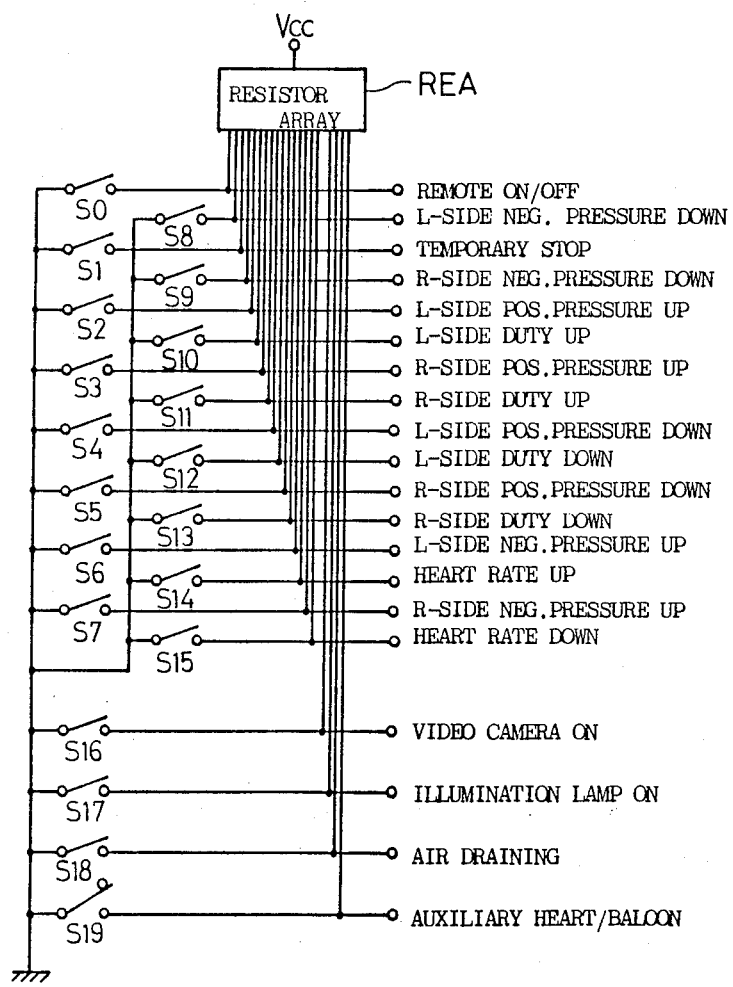
FIG. 13 is an electric circuit diagram showing the configuration of a body side control board MOB shown in FIG. 8.

FIG. 13 illustrates the configuration of the main body side control board MOB in FIG. 8. Description will now be made with reference to FIG. 13. The main body side control board MOB is composed of twenty switches S0 to S19 and a resistor array REA. The switches S0 to S15 have the same functions as the switches B0 to B15 equipped in the remote control board REM, respectively. The switches S0 to S19 function to instruct remote ON/OFF (whether or not the REM is made operable), temporary stop (operation of the solenoid valves 52, 53 and 56 is temporarily stopped), L-side positive pressure UP, R-side positive pressure UP, L-side positive pressure DOWN, R-side positive pressure DOWN, L-side negative pressure UP, R-side negative pressure UP, L-side negative pressure DOWN, R-side negative pressure DOWN, L-side duty UP, R-side duty UP, L-side duty DOWN, R-side duty DOWN, heart rate UP, heart rate DOWN, video camera ON, illumination lamp ON, air draining, and auxiliary heart/balloon pump selection, respectively.

Figure 14:
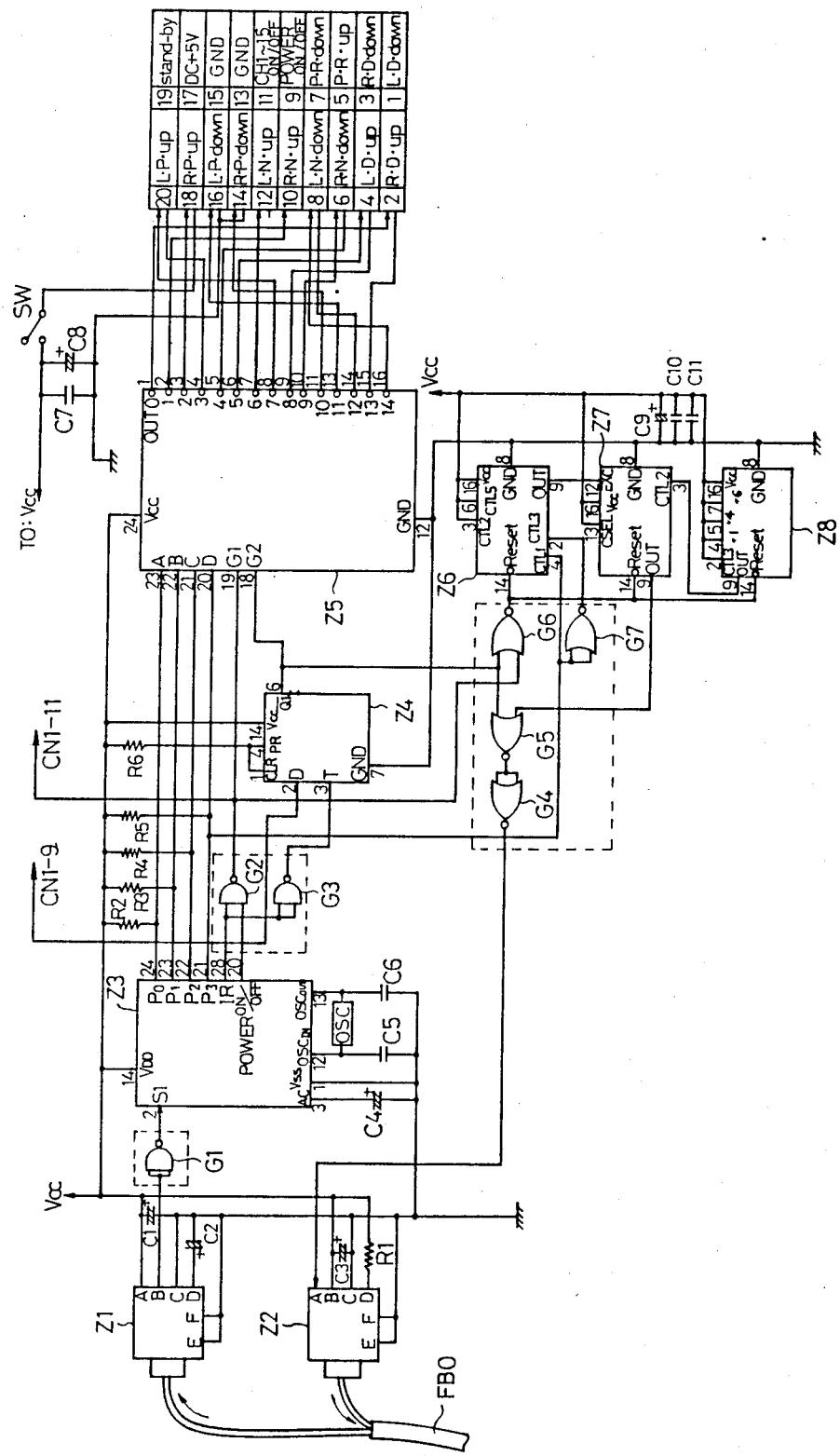
FIG. 14 is an electric circuit diagram showing the configuration of a remote controlling reception unit SRU shown in FIG. 8.
Figure 15:
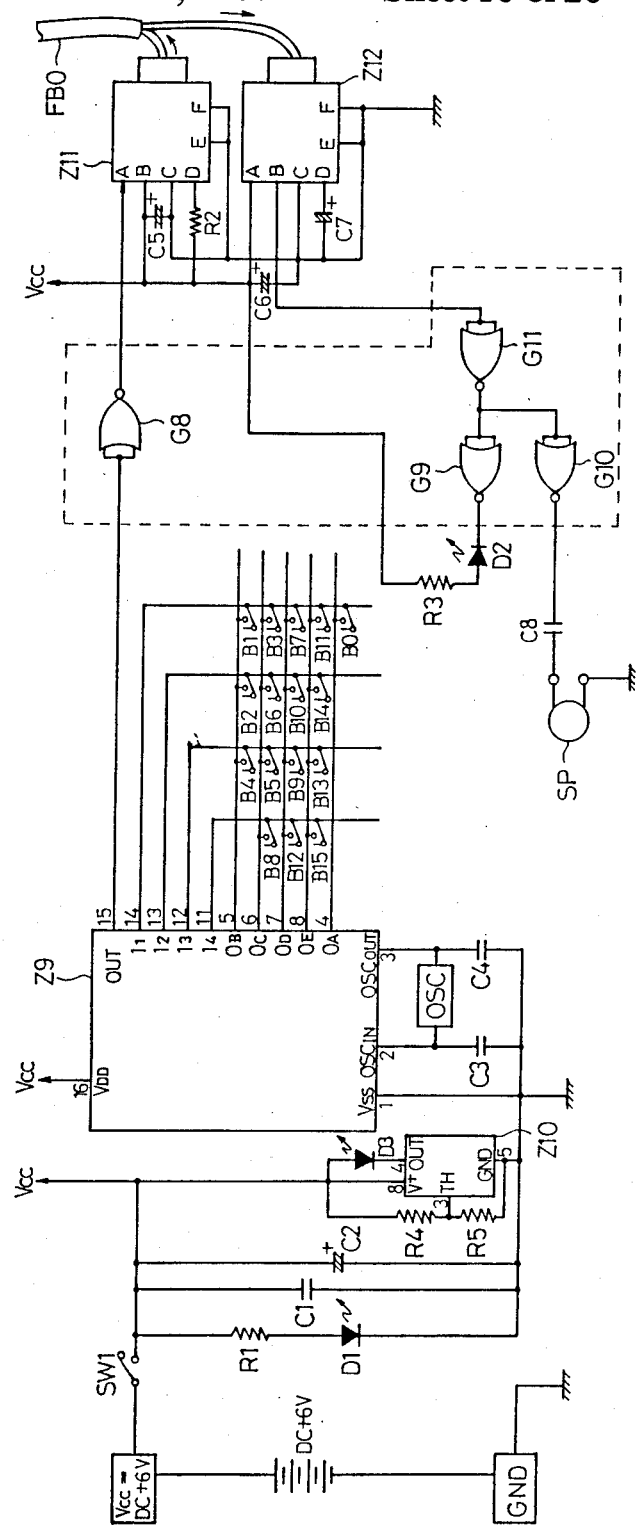
FIG. 15 is an electric circuit diagram showing the configuration of the remote control board REM.

FIG. 14 illustrates the circuit configuration of the signal receiving unit SRU for remote control in FIG. 8, and FIG. 15 illustrates the circuit configuration of the remote control board REM connected to the unit SRU. First, the remote control board REM will be described with reference to FIG. 15.

Designated at Z9 is an integrated circuit (M58484F manufactured by Mitsubishi Denki) for transmitting a remote control signal. Briefly stated, the integrated circuit Z9 includes a key scan signal generating circuit, a key input encoder, a command decoder, an oscillation circuit, a timing generating circuit, a code modulating circuit, an output buffer, etc., and it minitors 6×5 key matrix input terminals to discriminate 30 type instructions and outputs 6-bit PCM serial code data in accordance with the instruction.

The sixteen key switches B0 to B15 are connected in the form of a matrix to key scan output terminals Oa, Ob, Oc, Od and Oe and key input terminals $I_1$, $I_2$, $I_3$ and $I_4$ of the integrated circuit Z9. A battery is connected to a power supply terminal Vcc of the Z9 through a power supply switch SW1. Connected to the power supply line are a light emitting diode D1 for indicating power ON/OFF, capacitors C1, C2 for stabilizing voltage, an integrated circuit Z10, a light emitting diode D3 for indicating a drop in voltage, etc.

The integrated circuit Z10 is intended to monitor a drop in voltage and, in this embodiment, lights up the light emitting diode D3 when the voltage Vcc becomes below 4.3 V. Connected to a signal output terminal OUT of the integrated circuit Z9 is another integrated circuit Z11 through a logic gate G8. The integrated circuit Z11 is formed of an electro/photo conversion module (TOTX70 manufactured by Toshiba), and emits a beam of light in accordance with an electric signal applied to an input terminal A thereof.

One fiber of the optical fiber cable FBO is connected to a light output terminal of the integrated circuit Z11. The optical fiber cable FBO comprises a pair of optical fibers, and the other optical fiber of the FBO is connected to a light input terminal of an integrated circuit Z12. The integrated circuit Z12 is formed of an photo/electric conversion module (TORX70 manufactured by Toshiba). Connected to an electric signal output terminal B of the integrated circuit Z12 are logic gates G9 and G10 through a logic gate G11. A light emitting diode D2 is connected to an output terminal of the logic gate G9, and a speaker SP is connected to an output terminal of the logic gate G10 through a capacitor C8.

Next, the signal receiving unit SRC for remote control will be described with reference to FIG. 14. Designated at Z3 is an integrated circuit (M58481P manufactured by Mitsubishi Denki) for receiving a remote control signal. In brief, the integrated circuit Z3 includes an input circuit, a demodulation circuit, a command decoder, a timing generation circuit, a channel control circuit, an oscillation circuit, a flip-flop, etc., and it demodulates and decodes a signal applied to a transmission signal input terminal SI and then sets the result at output terminals $P_0$, $P_1$, $P_2$, $P_3$, IR, Power ON/OFF, etc. The output terminal IR issues a signal which indicates whether or not any signal has been received, i.e., whether or not any key input has been made on the transmitting side. The signal level at the output terminal Power ON/OFF is set or reset upon receiving a given signal (corresponding to operation of the switch B0 on the REM side) The output terminal is used herein for making remote control operable or inoperable.

Integrated circuits Z1 and Z2 are connected to the paired fibers of the optical fiber cable FBO. The integrated circuit Z1 is formed of a photo/electric conversion module (the same as Z12), and its light input terminal is connected to the light output terminal of the integrated circuit Z11 through the FBO. The integrated circuit Z2 is formed of an electro-photo conversion module (the same as Z11), and its light output terminal is connected to the light input terminal of the integrated circuit Z12 through FBO.

The received optical signal is converted to an electric signal and then applied from an output terminal B of the Z1 to the signal input terminal SI of the integrated circuit Z3 through a logic gate G1. An integrated circuit Z4 is formed of a D type flip-flop, and Z5 is formed of a decoder (74159). 4-bit code data obtained at output terminals $P_0$ to $P_3$ of the integrated circuit Z3 is decoded by the decoder Z15 to any one of 15 type instruction signals and then supplied to the respective circuits through a connector CN1. The decoder Z5 is formed to produce open collector outputs, and its output lines are connected to the corresponding signal lines of the main body side control board MOB through wired-OR logic.

The level at the output terminal Power ON/OFF of the integrated circuit Z3 is set into the flip-flop Z4 every when receiving an optical signal. Since an output signal from the flip-flop Z4 is applied to a gate input terminal G2 of the decoder Z5, the decode Z5 outputs no signal (which turns the transistor ON) when remote control is set to be inoperable.

Integrated circuits Z6, Z7 and Z8 are each of a programmable pulse generator. In brief, each pulse generator includes therein a quartz oscillator, a programmable divider, etc., and designated at CTL1 to CTL6 are frequency setting terminals, at OUT is an output terminal and at EXC is an input terminal for an external clock. In this example, when an optical signal is received with remote control being set to be operable, the integrated circuits Z6, Z7 and Z8 are released from the reset state so as to output pulse signals.

When released from the reset state, the Z8 applies a pulse signal of relatively long fixed period to the frequency control terminal CTL2 of the Z7. Further, a signal from the output terminal $P_3$ of the Z3 is applied to the frequency control terminals CTL1 and CTL3 of the Z6. In this example, transmission code is grouped depending on UP/DOWN of the control parameters, so that the signal level obtained at the output terminal $P_3$ of the integrated circuit Z3 becomes different between the case where any switch on the UP side of the remote control board is operated and the case where any switch on the DOWN side thereof is operated.

Accordingly, the frequency dividing ratio resulting from the integrated circuit Z6 is varied depending on the type (UP/DOWN) of switch. In this example, stated conclusively, signals of 3.3 KHz and 1.75 KHz alternately appear for each predetermined period of time when a change in parameter or temporary stop is instructed on the UP side, while signals of 1.70 KHz and 0.85 KHz alternately appeared when a change in parameter is instructed on the DOWN side. The signal is applied from the output terminal OUT of the integrated circuit Z7 to the integrated circuit Z2 through logic gates G5 and G4. In other words, when any switch is operated in the remote control board REM, the signal corresponding to that switch is transmitted in the form of an optical signal from the signal receiving unit SRU for remote control to the remote control board REM.

The transmitted optical signal is converted to an electric signal by the Z12 so as to energize the light emitting diode D2 and the speaker SP through the logic gates G11, G9 and G10. Therefore, it can be confirmed on the side of the remote control board REM using a light and sound, for example whether or not remote control is effected and whether the switch is operated on the UP side or the DOWN side.

Figure 16A:
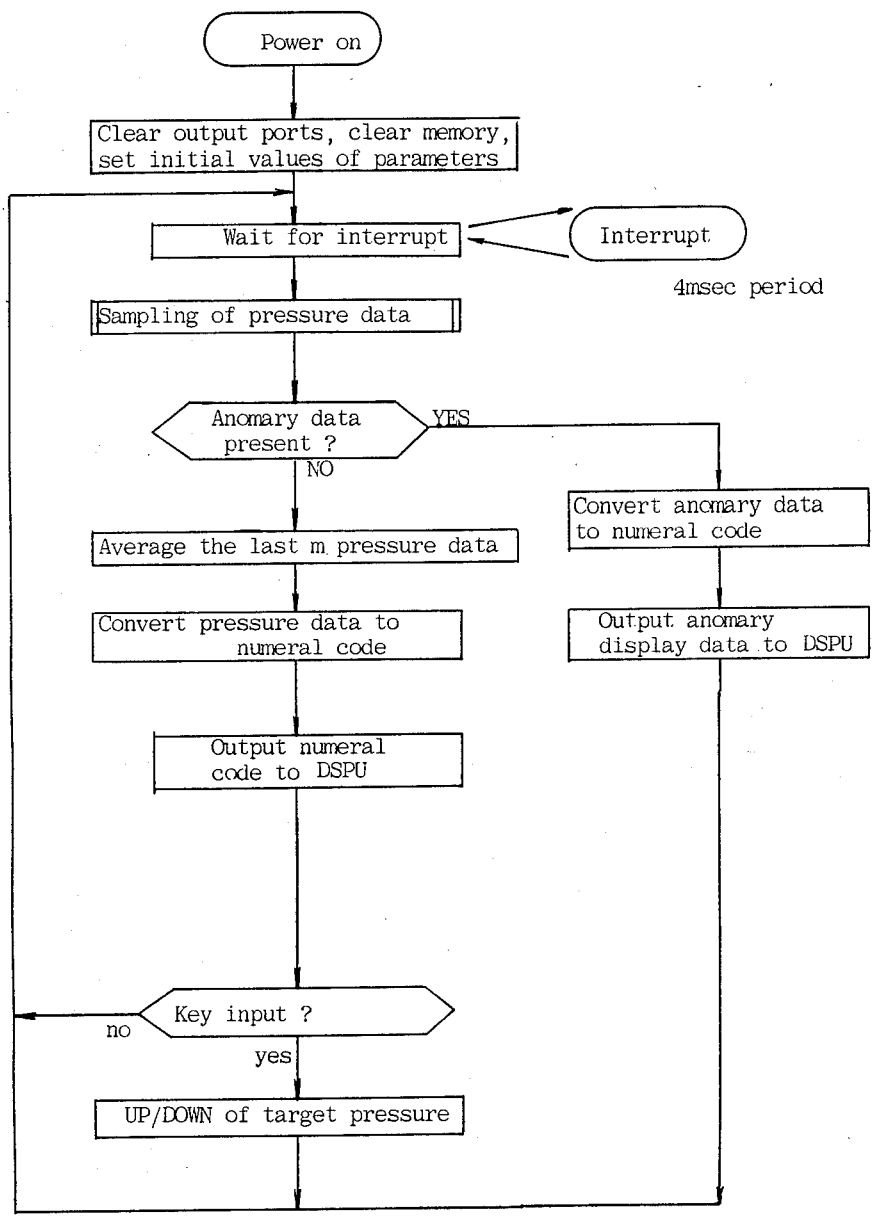

FIGS. 16a and 16b illustrate schematic operation of the microcomputer unit CPU1. FIG. 16a shows a main routine and FIG. 16b shows a interrupt processing routine. Description will now be made with reference to FIGS. 16a and 16b.

When powered-on, the CPU1 sets the output ports at initial levels, clears the content of a read/write memory (RAM), reads out the data previously stored in a read only memory (ROM) and then sets initial values to the respective parameters. As the parameters of the CPU1, there are a right side positive pressure goal value P1, a right side negative pressure goal value P2, a left side positive pressure goal value P3, a left side negative pressure value P4, etc. and, in this embodiment, the initial values of those pressures P1, P2, P3 and P4 are set equal to +30, −30, +100 and −50 (mmHg), respectively.

After the above processing, an interruption is allowed. In this embodiment, an interruption is cyclically caused by an internal timer at the period of 4 msec. After waiting for an interruption, pressure data is sampled. The sampled pressure data is checked, and the presence or absence of anomalous data is decided. In other words, it is assumed to be anomalous the case where the detected pressure is anomalously different from the goal value. In this embodiment, the solenoid valves 53 and 56 for compensating pressure are provided and there is a possibility that the pressure may become relatively large at moments. However, such a possibility is masked by sampling pressure data plural times and then averaging the sampled results.

If any anomaly should occur, anomalous data is converted to numeral code data, and anomaly indicating data which represents both the converted data and the part where an anomaly has occurred, is output to the display unit DSP and then displayed thereon.

If there is no anomaly, the past m pressure data stored in the read/write memory are averaged, the averaged data is converted to numerical data, and the coded data is sent to the display unit DSPU. When any key is operated on the main body side control board MOB or the remote control board REM, the value of right side positive goal pressure P1, right side negative goal pressure P2, left side positive goal pressure P3 or left side negative goal pressure P4 is updated by predetermined steps at a time depending on the operated key. It is to be noted that upper and lower limits are preset so as to prevent pressure setting out of the limited range.

The interrupt processing will now be described with reference to FIG. 16b. First, the CPU1 checks the positive pressure RPP in the right side artificial heart driving system. If the RPP is lower than the predetermined pressure P1, the pressure regulating valve 51(R) is set to be opened, and in the case other than the above, the pressure regulating valve 51(R) is set to be closed. Then, the negative pressure RNP in the right side artificial heart driving system is checked. If the value (absolute value) of the RNP is smaller than the P2, the pressure regulating valve 54(R) is set to be opened, and if not so, the pressure regulating valve 54(R) is set to be closed. Subsequently, the left side positive pressure LPP and negative pressure LNP are compared with the P3 and P4, respectively, whereby the pressure regulating valves 51(L) and 54(L) are set to be opened or closed. Stated differently, in this embodiment, only when the detected pressure (absolute value) is smaller than the goal pressure, the pressure regulating valve 51 or 54 is opened.

Figure 17A:
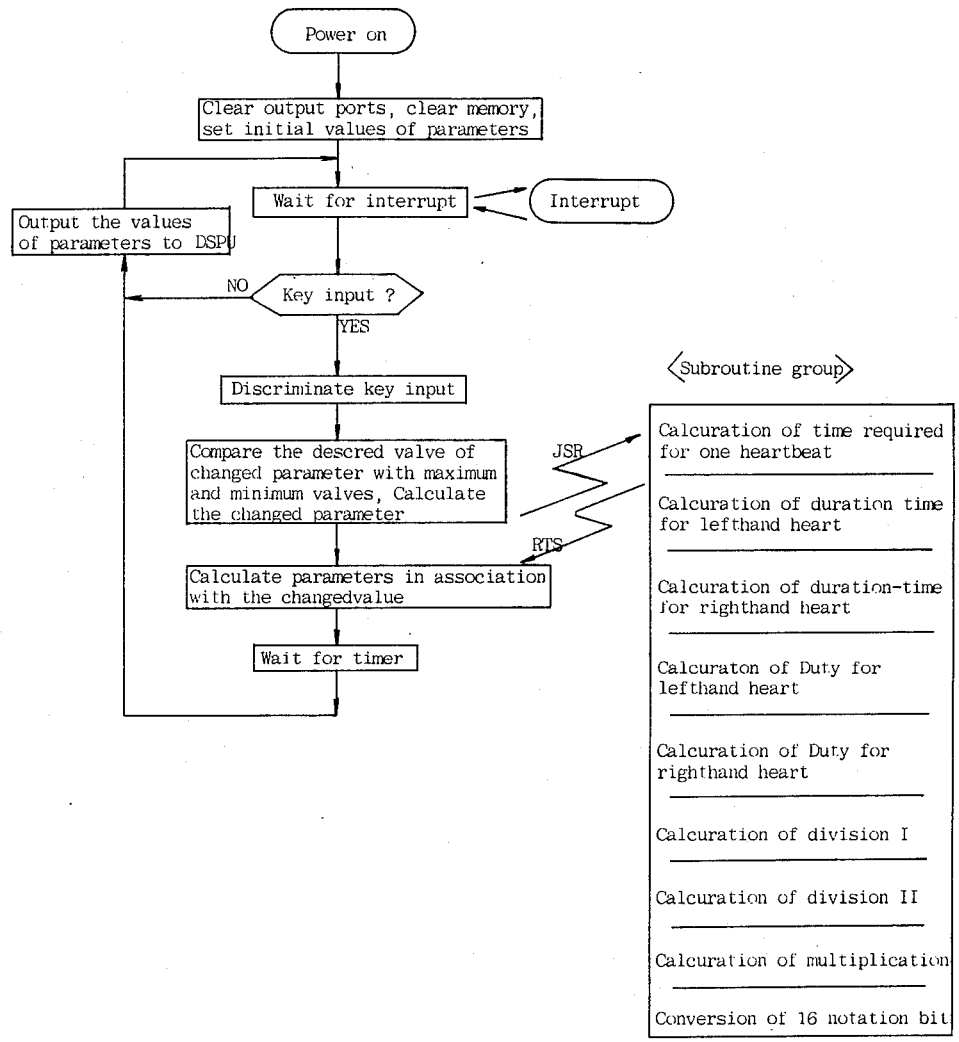
FIGS. 17a and 17b are flow charts showing schematic operation of the CPU2 in FIG. 10.
Figure 17B:
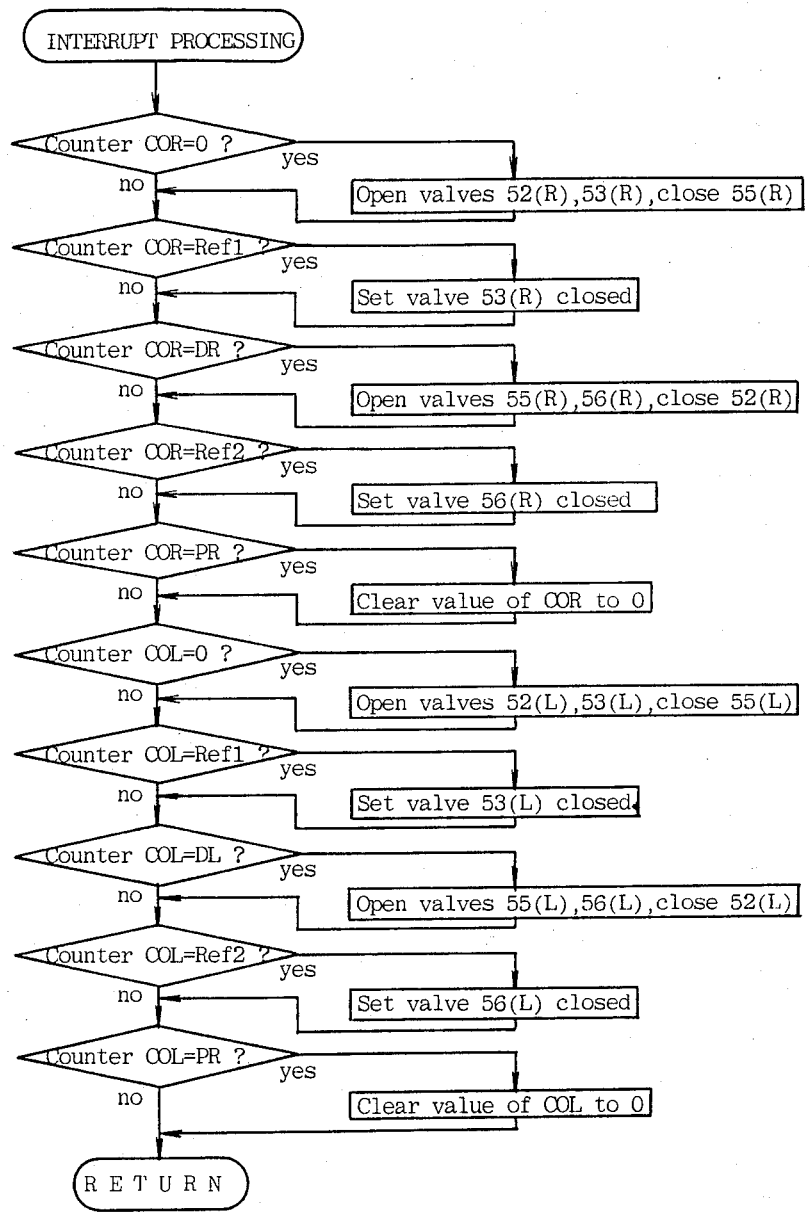

Schematic operation of the microcomputer CPU2 is shown in FIGS. 17a and 17b. FIG. 17a shows a main routine and FIG. 17b shows an interrupt processing routine. Description will now be made with reference to FIGS. 17a and 17b.

When powered-on, the microcomputer CPU2 sets the output ports to initial levels, clears the content of the read/write memory (RAM), reads out the data previously stored in the read only memory (ROM) and then sets initial values to the respective parameters.

As the parameters of the CPU2, there are heart rate PR, duty for the left side artificial heart DL, duty for the right side artificial heart DR, etc, and, in this embodiment, the initial values of those parameters PR, D1 and DR are set equal to 100 rpm, 45% (systolic duration 270 msec) and 55% (systolic duration 330 msec), respectively.

Then, the CPU2 executes a processing loop which includes processes such as waiting for an interruption, checking an key input from the control board, indicating the parameters, etc. If any key input is present, the type of the input key is judged, the desired value of changed parameter is computed to be compared with the upper and limit values, and parameters in association with the changed parameter is subjected to arithmetic computing process. These processes are performed while implementing various subroutines.

Interrupt processing will now be described. The values of counters COR and COL are counted up by one for each interrupt processing. When the counted value of each counter reaches the PR (time parameter determined by heart rate), it is cleared to 0. When the value of the counter COR becomes 0, the CUP2 sets the valves 52(R), 53(R) and 55 (R) to be opened, opened and closed (i.e., positive pressure applying mode), respectively. When the value of the counter COR reaches the reference value Ref1 (value for restricting the opening time of the positive pressure compensating solenoid valve 53), the solenoid valve 53(R) is set to be closed. When the value of the counter COR reaches the value DR of duty parameter, the CPU2 sets the valves 55(R), 56(R) and 52(R) to be opened, opened and closed (i.e., negative pressure applying mode), respectively. When the value of the counter COR reaches the reference value Ref2 (value for restricting the opening time of the negative pressure compensating solenoid valve 56), the solenoid valve 56(R) is set to be closed. After these processes, the counter COR is counted up.

Similarly, the CPU2 sets the valves 52(L), 53(L) and 55(L) to be opened, opened and closed (i.e., positive pressure applying mode), respectively, when the value of the counter COL becomes 0; sets the solenoid valve 53(L) to be closed, when the value of COL reaches the reference value Ref1 (value for restricting opening time of the positive pressure compensating solenoid valve 53); sets the valves 55(L), 56(L) and 52(L) to be opened, opened and closed (i.e., negative pressure applying mode), when the value of COL reaches the value DL of duty parameter; and sets the solenoid valve 56(L) to be closed and then counts up the COL, when the value of COL reaches the reference value Ref2 (value for restricting opening time of the negative pressure compensating solenoid valve 56).

Figure 19A:
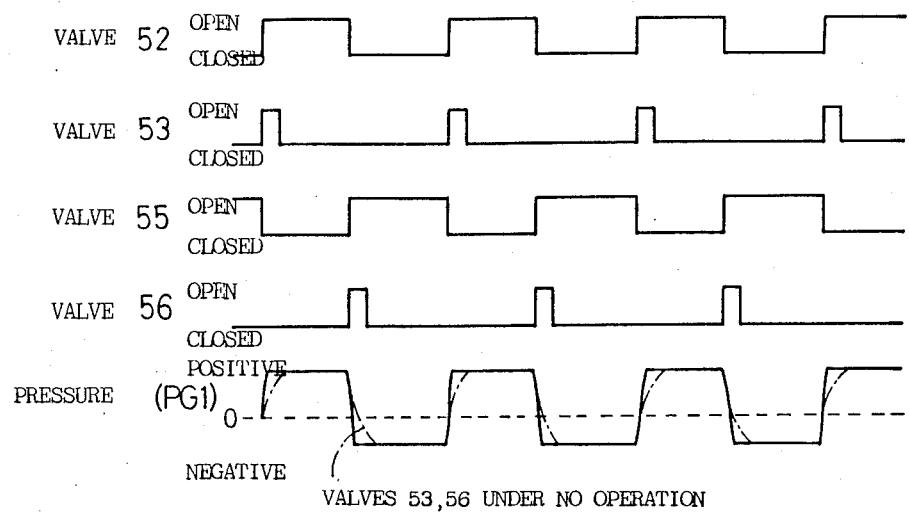
FIGS. 19a, 19b and 19c are waveform views showing operation timing in the apparatus.

In other words, the solenoid valves 52, 53, 55 and 56 are operated as shown in FIG. 19a. Since it is so controlled that the solenoid valve 53 is temporarily opened after switching from the negative pressure to the positive pressure and the solenoid valve 56 is opened after switching from the positive pressure to the negative pressure, rising and falling of pressure becomes sharp causing the waveform of pressure to be square. The solenoid valve 56 may be dispensed with, because the speed of switching (falling) from the positive pressure to the negative pressure produces no substantive influence upon drive of the artificial heart. Though not shown in FIGS. 17a and 17b, if temporary stop is instructed (i.e. S1 or B1 is turned ON), the CPU2 stops to drive the solenoid valves 52, 53, 55 and 56 during the time such instruction is present.

Figure 18A:
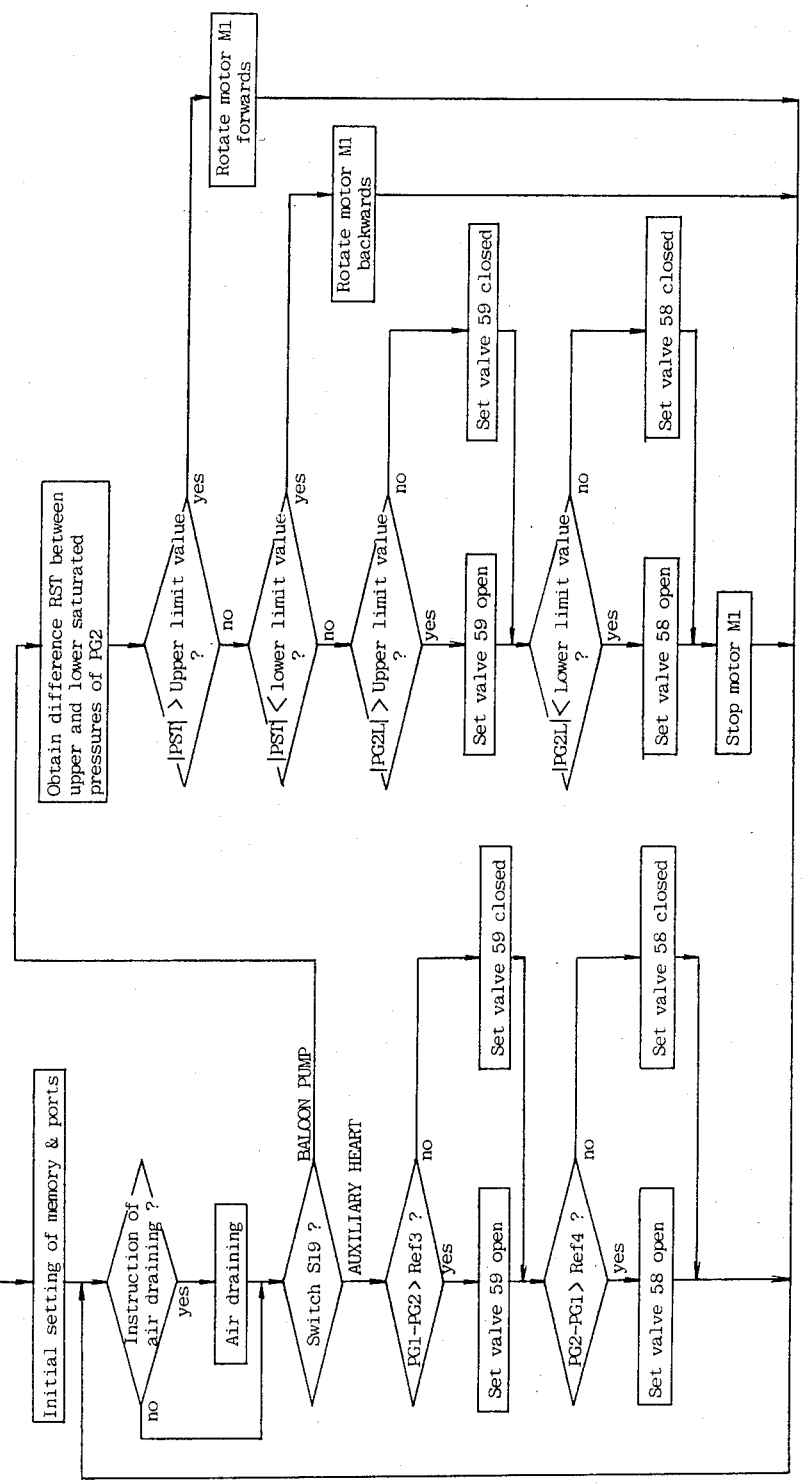
FIGS. 18a and 18b are flow charts showing schematic operation of the CPU3 in FIG. 11.
Figure 18B:
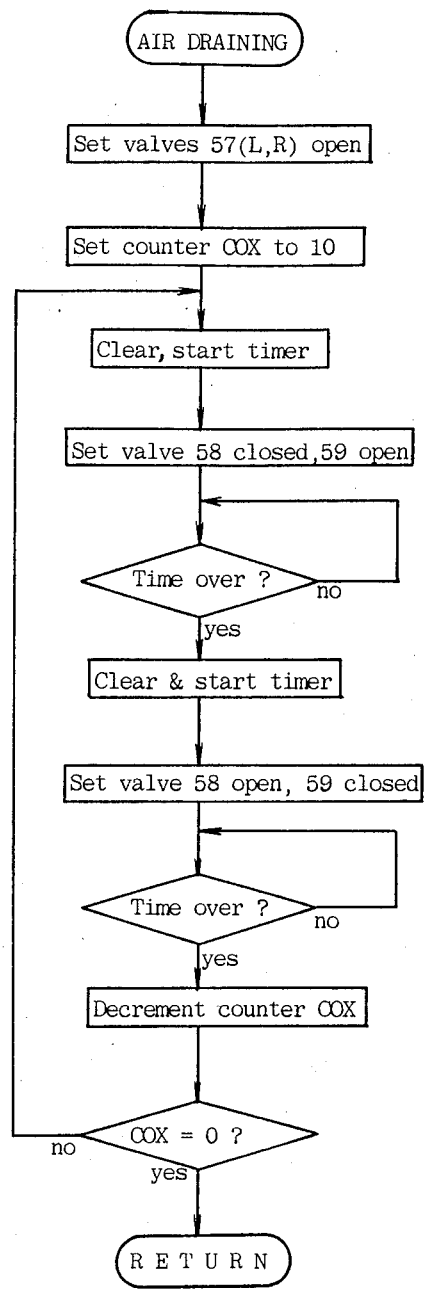

Schematic operation of the microcomputer unit CPU3 is shown in FIGS. 18a and 18b. FIG. 18a shows a main routine and FIG. 18b shows air exhausting subroutine.

First, description will be described with reference to FIG. 18a. When powered-on, the CPU3 makes initial setting of the memory and output ports, and then checks whether or not air draining is instructed (i.e., S18 is turned ON). If instructed, it implements the air draining subroutine described later. Further the CPU3 checks the state of the switch S19 to judge whether the right side driving system is in an auxiliary heart mode or a balloon pump mode.

In case of an auxiliary heart mode, the CPU3 reads output signals PG1 and PG2 from the pressure sensors PS3 and PS4. If the level of PG1 is larger than the level of PG2 by a predetermined value Ref3, the solenoid valve 59 is set to be opened and helium gas is supplied from the helium tank HTA to the secondary side of the fluid isolator AGA. Since relatively high (e.g., 150 mmHg) pressure appears at the output of the pressure reducing valve 61, the pressure on the secondary side of the AGA is raised up with the solenoid valve 59 being opened.

If the difference between PG1 and PG2 is less than the value Ref3, the solenoid valve 59 is set to be closed. Meanwhile, if the level of PG2 is larger than the level of PG1 by a predetermined value Ref4 or more, the solenoid valve 58 is set to be opened, thereby to reduce the secondary side pressure of the AGA. If the difference between PG1 and PG2 is less than a predetermined value, the solenoid valve 58 is set to be closed.

Figure 19B:
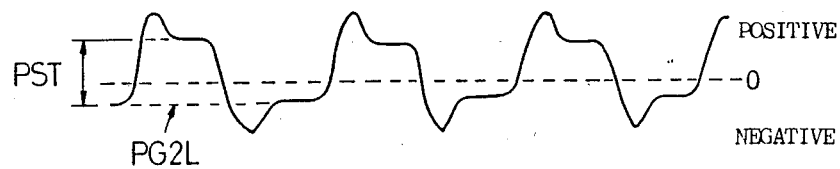
Figure 19C:
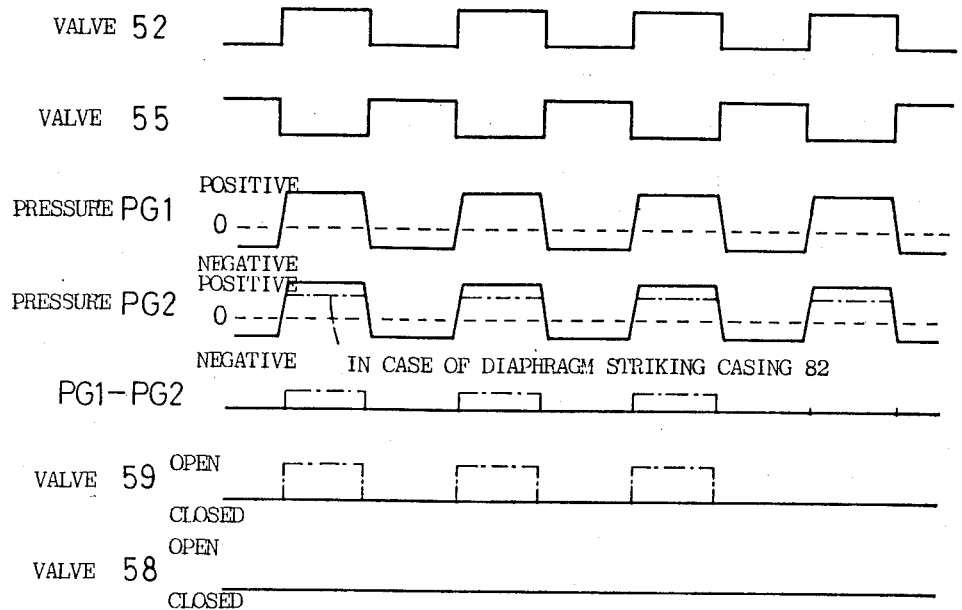

Operation timing in an auxiliary heart mode is shown in FIG. 19c. The plates 84 and 85 (including the diaphragm 83) of the fluid isolator AGA are normally vibrating in accordance with pressure changes from the air pressure controlling mechanism without striking the housings 81, 82 and the restriction member 63. In this state, there causes no substantive difference between the pressure on the primary side of the fluid isolator AGA and the pressure on the secondary side thereof.

However, if a fluid leak occurs on the secondary side of the fluid isolator AGA (i.e., helium gas leaks to the atmosphere side), the pressure on the secondary side is lowered to move the vibrating position of the plates 84, 85 rightwards in FIG. 6. When this movement exceeds a predetermined value, the plate 84 is brought into contact with the housing 82. With the plate 84 coming into contact with the housing 82, the fluid pressure on the secondary side of the fluid isolator AGA will not be raised up any more, so that there causes a difference between the pressure PG1 on the primary side and the pressure PG2 on the secondary side.

After opening of the solenoid valve 59, if the secondary side pressure PG2 of the AGA is increased to move the vibrating position of the plates 84, 85 leftwards in FIG. 6 and this movement exceeds a predetermined value, the plate 85 is brought into contact with the restriction member 63 or the housing 81, thus producing the relationship of PG1<PG2. Therefore, by controlling the solenoid valves 58 and 59 to maintain the difference between PG1 and PG2 less than a predetermined value as mentioned above, it becomes possible to drive the fluid isolator while holding the secondary side pressure PG2 within a predetermined range, so that the plates 84, 85 will not stop vibrations.

When the switch S19 is set on the balloon pump side, a balloon mode is effected. Stated briefly, in a balloon side, the CPU3 monitors only the secondary side pressure PG2 and then controls the solenoid valves 58, 59 and the motor M1 so that the stroke of the plates 84 and 85 will vibrate within a positional range defined by the housing 82 and the restriction member 63.

In this mode, the pressure PG2 has the waveform as shown in FIG. 19b. More specifically, when the driving pressure is changed from the negative pressure to the positive pressure, the pressure equal to PG1 first appears as PG2 and, at the time when the plate 84 comes into contact with the housing 82, the pressure start to be lowered (saturated). Meanwhile, when the driving pressure is changed from the positive pressure to the negative pressure, the pressure equal to PG1 first appears as PG2 and, at the time when the plate 85 comes into contact with the restriction member 63, the pressure starts to rise (saturate) (the absolute value is reduced).

Returning back to FIG. 18a, the difference between the upper and lower saturated pressures of PG2, i.e., PST in FIG. 19b, is first obtained. The PST corresponds to the movable range (stroke) of the plates 84, 85. If the PST is larger than the upper limit value of stroke, the motor M1 is driven to rotate forwards causing the restriction member 63 to be driven rightwards in FIG. 6, while if the PST is smaller than the lower limit value of stroke, the motor M1 is driven to rotate backwards causing the restriction member 63 to be driven leftwards in FIG. 6. In this way, at first the stroke of the plates 84, 85 is regulated within a predetermined range.

Stroke regulation is necessary from the following reasons. One is in that, since capacity of the balloon pump is different depending on a physique of the patient (adult, child, etc.), the stroke should be reduced to eliminate the useless operation, thus making the balloon pump to move easily, when a balloon pump of small capacity is driven. The other is in limiting an amount of discharged gas to a small extent, if the balloon pump should burst.

Subsequently, the negative side saturated pressure PG2L (absolute value) is compared with the preset upper and lower values. If the PG2L is larger than the upper limit value, the solenoid valve 59 is set to be opened, while if it is smaller than the upper limit value, the solenoid valve 59 is set to be closed. If the PG2L is smaller than the lower limit value, the solenoid valve 58 is set to be opened, while if it is larger than the lower limit value, the solenoid valve 58 is set to be closed. This maintains the PG2L between the upper limit value and the lower limit value, and it is so controlled that an amount of helium gas on the secondary side of the fluid isolator AGA will not be changed greatly.

Next, air exhausting operation will be described. When the switch S18 is turned ON, the CPU3 implements the air exhausting subroutine. Description will now be made with reference to FIG. 18b. In this embodiment, the solenoid valves 57(R, L) are first opened to make the primary side of the fluid isolator AGA open to the atmosphere. Then, a predetermined value (10 in this embodiment) is set in a counter COX (internal register). The timer is cleared and started, and the solenoid valves 58 and 59 are set to be closed and opened, respectively. When the timer reaches the present time, the solenoid valves 58 and 59 are closed and opened, respectively, after clearing and starting the timer. When the timer again reaches the preset time, the counter COX is decremented. If the COX is not equal to 0, the above processes are repeated.

In other words, for each predetermined time preset in the timer, the solenoid valves 58 and 59 are repeatedly opened and closed and then closed and opened, respectively. Therefore, the positive and negative pressures are alternately applied to the secondary side of the fluid isolator AGA and, since the primary side of the fluid isolator AGA is under the atmospheric pressure, the plates 84 and 85 are reciprocally moved between two positions that are defined by the housings 81, 82 and the restriction member 63. As a result, a large amount of fluid alternately goes in and comes out from a passage on the secondary side of the AGA, so that the fluid inside the passage is gradually replaced from air to helium gas.

Accordingly, even if the tube of the balloon pump 60B is mounted to the body of the driving apparatus in the normal room, air present on the secondary side of the fluid isolator AGA can be exhausted by simple switch operation.

Figure 20:
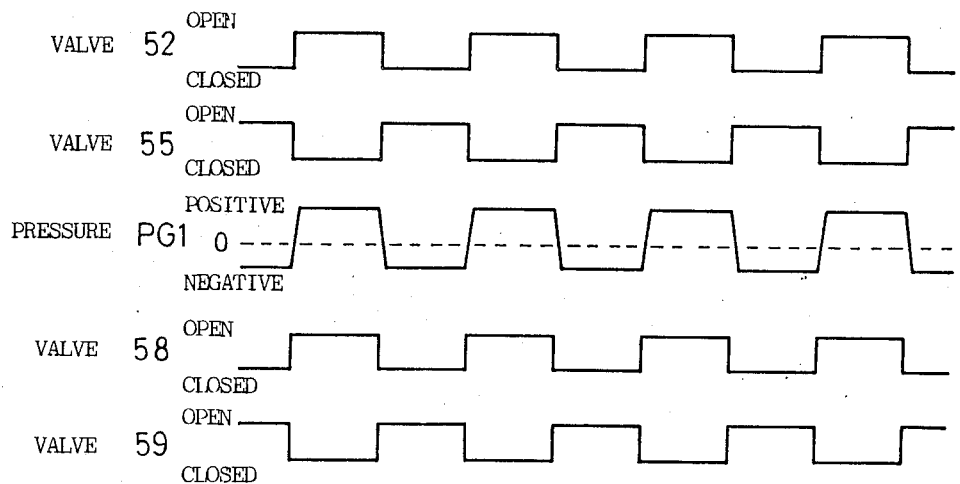
FIG. 20 is a waveform view showing operation timing in another embodiment of the present invention.

Although, in the above embodiment, the solenoid valve 57 is provided on the primary side of the fluid isolator AGA to exhaust from the secondary side of the AGA, the solenoid valve 57 can be dispensed with if the solenoid valves 58 and 59 are controllably opened and closed in synchronous relation with the sclenoid valves 52 and 55 in the air pressure controlling mechanism. The operation timing in such a case is shown in FIG. 20. More specifically, the solenoid valve 58 may be opened to drive the plates 84, 85 toward the secondary side at the timing when the solenoid valve 52 is opened to apply the positive pressure to the primary side of the AGA, and the solenoid valve 59 is opened to drive the plates 84, 85 toward the secondary side of the AGA at the timing when the solenoid valve 55 is opened to apply the negative pressure to the primary side of the AGA.

Figure 22A:
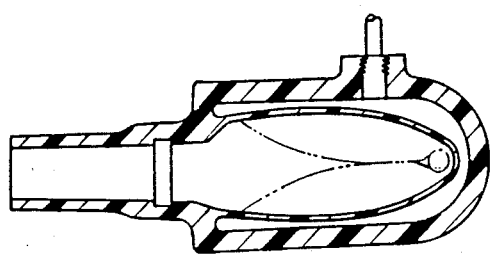
FIGS. 22a and 22b are a longitudinal sectional view and a transverse sectional view showing the mounted positions of the optical fibers FB1, FB2 to the artificial heart in another modified embodiment, respectively.
Figure 22B:
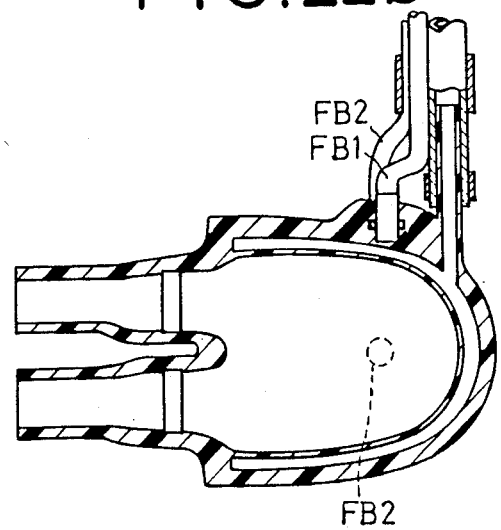

FIGS. 21a and 29b as well as FIGS. 22a and 22b show modified embodiments where mounting positions of the optical fiber FB1 connected to the video camera and the optical fiber FB2 connected to the illumination lamp are changed. It is to be noted that, although the foregoing embodiment has been described with reference to the case an artificial heart, etc. is driven with helium gas, another gas such as carbon dioxide may be used an alternative.

According to the embodiment as mentioned above, since an artificial heart, etc. is driven using a fluid such as helium gas that is not harmful to the human body, safety is ensured if the worst should happen. Furthermore, by using the pressure compensating solenoid valve 53, an artificial heart, etc. can be driven under the preferable pressure condition.

What we claim is:

1. An apparatus for driving a medical appliance comprising:
    setting means provided with a plurality of switches
    a first pressure regulating device comprising a positive pressure source, a first solenoid valve having an input terminal connected to an output terminal of said positive pressure source, a negative pressure source, a second solenoid valve having an input terminal connected to an output terminal of said negative pressure source and an output terminal connected to an output terminal of said first solenoid valve, and first electronic control means for controllably opening and closing said first and second solenoid valves in accordance with the setting values preset by said setting means, the output terminal of said first solenoid valve serving as an output terminal of said first pressure regulating device; and a second pressure regulating device comprising medical appliance driving means having an input terminal and an output terminal separated by a diaphragm shiftable in a predetermined range in accordance with the applied pressure, first pressure detecting means disposed on at least the output side of said medical appliance driving means, gas supplying means, a third solenoid valve having an output terminal connected to the output side of said medical appliance driving means and an input terminal connected to an output terminal of said gas supplying means, and second electronic control means for controlling energization of said third solenoid valve in accordance with both the setting values preset by said setting means and an output signal from said first pressure detecting means, the input terminal of said medical appliance driving means being connected to the output terminal of said first pressure regulating device and the output terminal of said medical appliance driving means being connected to said medical appliance wherein said positive pressure source is provided with a fourth solenoid valve inserted in a flow passage thereof and second pressure detecting means for detecting pressure at an output terminal of said fourth solenoid valve, said negative pressure source is provided with a fifth solenoid valve inserted in a flow passage thereof and third pressure detecting means for detecting pressure at an output terminal of said fifth solenoid valve, and said first electronic control means controls said fourth solenoid valve in accordance with both the positive pressure setting value preset by said setting means and an output signal from said second pressure detecting means, and also controls said fifth solenoid valve in accordance with the negative pressure setting value preset by said setting means and an output signal from said third pressure detecting means and wherein said first pressure regulating device includes a sixth solenoid valve connected between the output terminal of said first pressure regulating device and an input terminal of said fourth solenoid valve, and said first electronic control means controllably opens and closes said sixth solenoid valve at the given timing in synchronous relation with the control timing of said first solenoid valve.

2. An apparatus for driving a medical appliance according to claim 1, wherein said first pressure regulating device includes a seventh solenoid valve connected between the output terminal of said first pressure regulating device and an input terminal of said fifth solenoid valve, and said first electronic control means controllably open and close said seventh solenoid valve at the given timing in synchronous relation with the control timing of said second solenoid valve.

3. An apparatus for driving a medical appliance according to claim 1, wherein said first pressure regulating device includes at least two accumulators, the output terminal of said positive pressure source and the input terminal of said first solenoid valve are open to the inside of a first accumulator, and the output terminal of said negative pressure source and the input terminal of said fourth solenoid valve are open to the inside of a second accumulator.

4. An apparatus for driving a medical appliance according to claim (1), wherein said second pressure regulating device includes an eighth solenoid valve having one end connected to the output side of said medical appliance driving means and the other end connected to a pressure below the atmospheric pressure.

5. An apparatus for driving a medical appliance according to claim 3, wherein said second pressure regulating device includes an eighth solenoid valve having one end connected to the output side of said medical appliance driving means and the other end open to the inside of said accumulator in the negative pressure system of said first pressure regulating device.

6. An apparatus for driving a medical appliance according to claim 4, wherein said second electronic control means further includes means for setting the pressure on the input side of said medical appliance driving means to atmospheric pressure when a first instruction is applied from said setting means thereby to alternately repeat the state where said third solenoid valve is opened and said eighth solenoid valve is closed and the state where said third solenoid valve is closed and said eighth solenoid valve is opened.

7. An apparatus for driving a medical appliance according to claim 6, wherein said second pressure regulating device includes a ninth solenoid valve having one end disposed on the input side of said medical appliance driving means and the other end connected to the atmosphere, and said second electronic control means opens the other end of said ninth solenoid valve to the atmosphere when said first instruction is applied.

8. An apparatus for driving a medical appliance according to claim 4, wherein, when said first instruction is applied, said second electronic control means includes means for switching the states of said third solenoid valve and said eighth solenoid valve in synchronous relation with operations of said first solenoid valve and said second solenoid valve.

9. An apparatus for driving a medical appliance according to claim 1, wherein input terminals of two pressure regulating devices are connected to an output terminal of one first pressure regulating device, and said second electronic control means selectively controls either one of said two second pressure regulating devices in accordance with the given instruction from said setting means.

10. An apparatus for driving a medical appliance according to claim 1, wherein said first pressure detecting means comprises a plurality of pressure detecting means disposed on both the input and output sides of said medical appliance driving means, and said second electronic control means controls said third solenoid valve in accordance with the difference between an output signal from said first pressure detecting means on the input side and an output signal from said first pressure detecting means on the output side.

11. An apparatus for driving a medical appliance according to claim 1, wherein said medical appliance driving means includes a movable portion for restricting a shiftable range of said diaphragm and electric control driving means for driving said movable portion, and said second electronic control means drives said electric control driving means and said third solenoid valve in accordance with the pressure on the output side of said medical appliance driving means.

12. An apparatus for driving a medical appliance according to claim, further including two sets of first pressure regulating devices and three sets of second pressure regulating devices.

13. An apparatus for driving a medical appliance comprising:
setting means provided with a plurality of switches;
a first pressure regulating device comprising a positive pressure source, a first solenoid valve having an input terminal connected to an output terminal of said positive pressure source, a negative pressure source, a second solenoid valve having an input terminal connected to an output terminal of said negative pressure source and an output terminal connected to an output terminal of said first solenoid valve, and first electronic control means for controllably opening and closing said first and second solenoid valves in accordance with the setting values preset by said setting means, the output terminal of said first solenoid valve serving as an output terminal of said first pressure regulating device; and
a second pressure regulating device comprising medical appliance driving means having an input terminal and an output terminal separated by a diaphragm shiftable in a predetermined range in accordance with the applied pressure, gas supplying means, a third solenoid valve having one end connected to the output side of said medical appliance driving means and the other end connected to said gas supplying means, a fourth solenoid valve having one end connected to the output side of said medical appliance driving means and the other end open to the atmosphere or connected to the negative pressure system, and second electronic control means connected to said third and fourth solenoids for setting the pressure on the input side of said medical appliance driving means to atmospheric pressure and then controllably opening and closing said third and fourth solenoid valves, when a first instruction is applied thereto, the input terminal of said medical appliance driving means being connected to the output terminal of said first pressure regulating device and the output terminal of said medical appliance driving means being connected to said medical appliance wherein said second electronic control means further includes means for setting the pressure on the input side of said medical appliance driving means to a different state when said first instruction is applied from said setting means thereby to alternately repeat the state where said third solenoid valve is opened and a fourth solenoid valve is closed and the state where said third solenoid valve is closed and said fourth solenoid valve is opened.

14. An apparatus for driving a medical appliance according to claim 13, wherein said second pressure regulating device includes a fifth solenoid valve having one end connected to the input side of said medical appliance driving means and the other end connected to the atmosphere, and said second electronic control means opens the other end of said fifth solenoid valve to the atmosphere when said first instruction is applied.

15. An apparatus for driving a medical appliance according to claim 13, wherein, when said first instruction is applied, said second electronic control means switches the states of said third and fourth solenoid valves in synchronous relation with operations of said first and second solenoid valves.

16. An apparatus for driving a medical appliance comprising:
setting means provided with a plurality of switches;
a first pressure regulating device comprising a positive pressure source, a first solenoid valve having an input terminal connected to an output terminal of said positive pressure source, a negative pressure source, a second solenoid valve having an input terminal connected to an output terminal of said negative pressure source and an output terminal connected to an output terminal of said first solenoid valve and first electronic control means operably connected to said first and second solenoid valves for controlling the opening and closing of said first and second solenoid valves in accordance with the setting values preset by said setting means, the output terminal of said first solenoid valve serving as an output terminal of said first pressure regulating device;
a second pressure regulating device comprising medical appliance driving means having an input terminal and an output terminal separated by a diaphragm shiftable in a predetermined range in accordance with the applied pressure and including a moveable portion for restricting a shiftable range of said diaphragm and electrically controlled driving means for driving said moveable portion, gas supplying means, a third solenoid valve having one end connected to the output side of said medical appliance driving means and the other end connected to said gas supplying means, a fourth solenoid valve having one end connected to the output side of said medical appliance driving means and the other end connected to an output side of said negative pressure system, pressure detecting means disposed on at least the output side of said medical appliance driving means; and
second electronic control means connected to said third and fourth solenoids for setting the pressure on the input side of said medical appliance driving means to atmospheric pressure and then controlling the opening and closing of said third and fourth solenoid valve when a first instruction is supplied thereto for alternately repeating the state where said third solenoid valve is open and said fourth solenoid valve is closed and the state where said third solenoid valve is closed and the fourth solenoid valve is open, said second electronic control means controlling said third and fourth solenoid valves in accordance with both the setting values preset by said setting means and an output signal from said pressure detecting means when a second instruction is applied thereto and controlling said electrically controlled driving means and said third solenoid valve in accordance with the pressure on the output side of said medical appliance driving means when a third instruction is applied thereto.

* * * * *